(12) United States Patent  (10) Patent No.: US 6,571,119 B2
Hayashi  (45) Date of Patent: *May 27, 2003

(54) FLUORESCENCE DETECTING APPARATUS

(75) Inventor: Katsumi Hayashi, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/893,395

(22) Filed: Jun. 29, 2001

(65) Prior Publication Data

US 2001/0049473 A1 Dec. 6, 2001

Related U.S. Application Data

(60) Continuation-in-part of application No. 09/538,481, filed on Mar. 30, 2000, now abandoned, which is a continuation of application No. 09/025,863, filed on Feb. 19, 1998, now Pat. No. 6,070,096, which is a division of application No. 08/812,770, filed on Mar. 6, 1997, now Pat. No. 5,833,617.

(30) Foreign Application Priority Data

Mar. 6, 1996 (JP) ............................................. 8-48782
Feb. 13, 1997 (JP) ............................................. 9-28928

(51) Int. Cl.$^7$ ................................................ A61B 6/00
(52) U.S. Cl. ..................................... 600/477; 250/458.1
(58) Field of Search ................................ 600/476, 477, 600/478, 160; 356/317, 318; 250/461.1, 458.1, 363.01, 362

(56) References Cited

U.S. PATENT DOCUMENTS

| 4,556,057 A | * 12/1985 | Hiruma et al. ............ 128/303.1 |
| 4,768,513 A | * 9/1988 | Suzuki ....................... 128/634 |
| 5,042,494 A | 8/1991 | Alfano ........................ 128/665 |
| 5,131,398 A | * 7/1992 | Alfano et al. ................ 128/665 |
| 5,348,018 A | 9/1994 | Alfano et al. ................ 128/665 |
| 5,421,337 A | 6/1995 | Richards-Kortum et al. ............................ 128/665 |
| 5,456,252 A | 10/1995 | Vari et al. ..................... 128/633 |
| 5,467,767 A | 11/1995 | Alfano et al. ................ 128/665 |
| 5,507,287 A | 4/1996 | Palcic et al. ................. 128/633 |
| 5,562,100 A | 10/1996 | Kittrell et al. ............... 128/665 |

(List continued on next page.)

FOREIGN PATENT DOCUMENTS

| JP | 1-136630 | 5/1989 | ............ A61B/5/00 |
| JP | 3-58729 | 9/1991 | ............ A61B/5/00 |
| JP | 7-59783 | 3/1995 | ............ A61B/10/00 |

OTHER PUBLICATIONS

"Fluorescence Imaging Of Early Lung Cancer," Annual International Conference of the IEEE Engineering in Medicine and Biology Society, vol. 12, No. 3, 1990.
"Fluorescence Imaging Diagnosis Of Cancer Using Red/Green Ratio" by Tokyo Medical College and Hamamatsu Photonics K.K., 16$^{th}$ Symposium of the Japanese Society of Laser Medical Science, 1995.

Primary Examiner—Shawna J. Shaw
(74) Attorney, Agent, or Firm—Sughrue Mion, PLLC

(57) ABSTRACT

When a fluorescence image is to be displayed, a region of interest in a living body is irradiated with excitation light so that the fluorescence emitted therefrom is detected by a cold CCD camera via image fibers. A color mosaic filter is fixed on the detection surface of the cold CCD camera so that the fluorescence is separated into three fluorescence components corresponding to red, green and blue wavelength ranges before being detected. The signal intensity corresponding to the red wavelength range is divided by the total signal intensity which is the sum of the signal intensities corresponding to the red, green and blue wavelength ranges. A visual image displayed on the monitor is based on thus divided signal intensity. As it is quite rare that the total signal intensity becomes zero, occurrence of an operation error due to division by the value of zero can be restrained.

9 Claims, 11 Drawing Sheets

U.S. PATENT DOCUMENTS

| | | | |
|---|---|---|---|
| 5,590,660 A | | 1/1997 | MacAulay et al. .......... 128/664 |
| 5,647,368 A | * | 7/1997 | Zeng et al. .................. 128/665 |
| 5,749,830 A | * | 5/1998 | Kaneko et al. .............. 600/160 |
| 5,769,792 A | | 6/1998 | Palcic et al. ................. 600/477 |
| 5,827,190 A | | 10/1998 | Palcic et al. ................. 600/476 |
| 5,833,617 A | * | 11/1998 | Hayashi ....................... 600/476 |
| 5,849,595 A | | 12/1998 | Alfano et al. ................ 436/164 |
| 5,865,754 A | | 2/1999 | Sevick-Muraca et al. ... 600/476 |
| 6,070,096 A | * | 5/2000 | Hayashi ....................... 600/477 |
| 6,196,226 B1 | * | 3/2001 | Hochman et al. ........... 600/425 |

* cited by examiner

F I G. 7
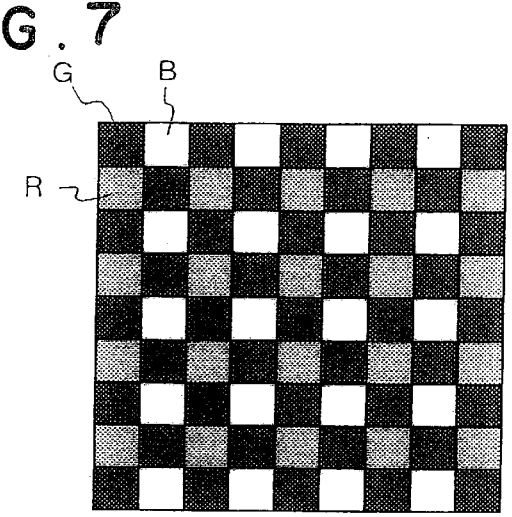
F I G. 8
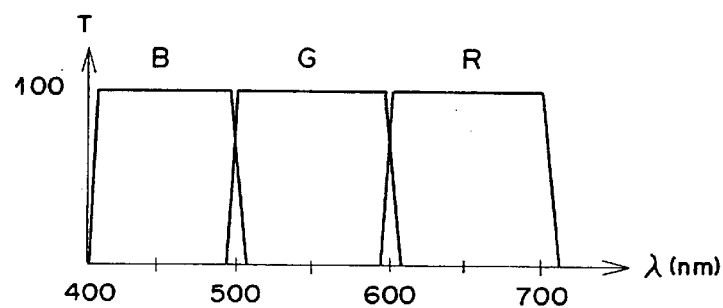
F I G. 9
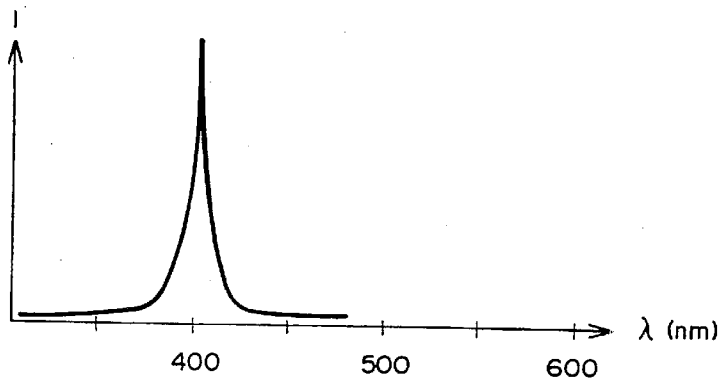

F I G.13
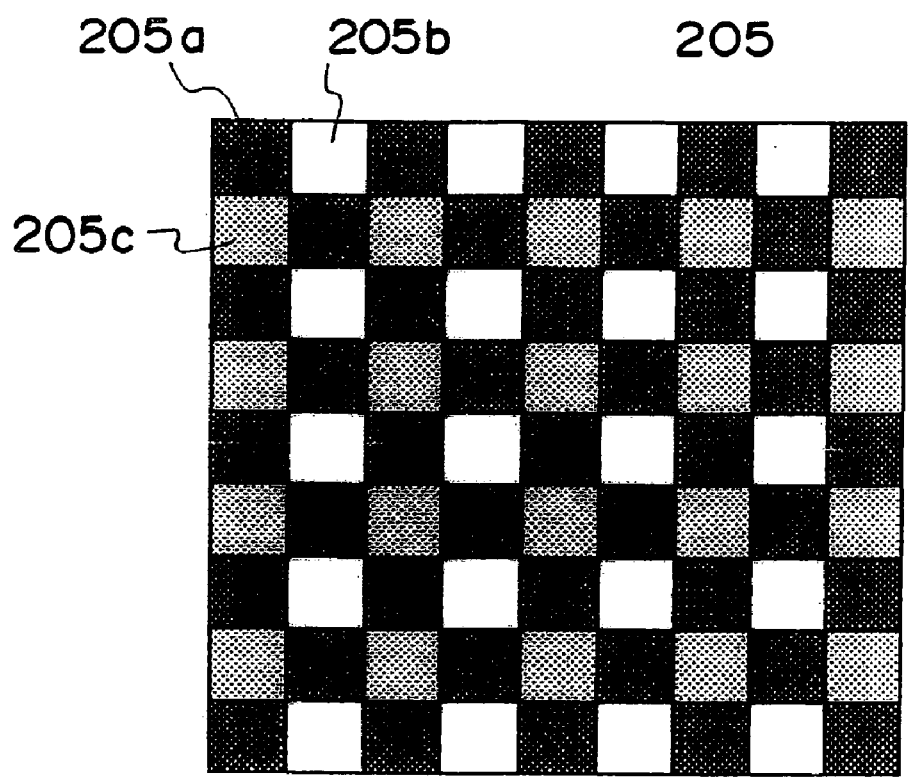

FLUORESCENCE DETECTING APPARATUS

This is a Continuation-in-Part of application Ser. No. 09/538,481 filed Mar. 30, 2000 now abandoned, which is a continuing application of application Ser. No. 09/025,863, filed Feb. 19, 1998, now U.S. Pat. No. 6,070,096, which is a divisional of application Ser. No. 08/812,770, filed Mar. 6, 1997, now U.S. Pat. No. 5,833,617. The disclosures of each of these preceding applications are incorporated into the present application by reference.

BACKGROUND OF THE INVENTION

1. Field of the Invention

This invention relates to a fluorescence detecting apparatus suitable for use in a fluorescence diagnosing system; wherein a diagnosis of a tumor is carried out by irradiating excitation light to a region of interest in a living body, to which a photosensitive substance, that has a strong affinity for the tumor and is capable of producing fluorescence when it is excited with the excitation light, has been administered, and by detecting the intensity of fluorescence, which is produced by the photosensitive substance and an intrinsic dye in the living body when the region of interest in the living body is exposed to the excitation light; or wherein a diagnosis of a tumor is carried out by irradiating excitation light to a region of interest in a living body, to which no photosensitive substance has been administered, and by detecting the intensity of intrinsic fluorescence, which is produced by an intrinsic dye in the living body when the region of interest in the living body is exposed to the excitation light.

2. Description of the Related Art

Extensive research has heretofore been conducted on the so-called photodynamic diagnosis (PDD) technique. With the PDD technique, a photosensitive substance (such as ATX-S10, 5-ALA, NPe6, HAT-DO1 or Photofrin-2), which has an affinity for a tumor and is capable of producing fluorescence when it is excited with light, is employed as a fluorescent diagnosis drug. The photosensitive substance is administered to a living body and is absorbed by a tumor part, such as a cancer, of the living body. Excitation light, which has wavelengths falling within the excitation wavelength range for the photosensitive substance, is then irradiated to the region containing the tumor part, and fluorescence is thereby produced from the fluorescent diagnosis drug having been accumulated at the tumor part. By the detection of the fluorescence, the location and infiltration range of the diseased part is displayed as an image, and the displayed image is used in conducting a diagnosis of the tumor part.

Fluorescence diagnosing systems for carrying out the PDD technique have been disclosed in, for example, U.S. Pat. No. 4,556,057, and Japanese Unexamined Patent Publication Nos. 1(1989)-136630 and 7(1995)-59783. Basically, each of the disclosed fluorescence diagnosing systems comprises: an excitation light irradiating means for irradiating excitation light, which has wavelengths falling within the excitation wavelength range for a photosensitive substance, to a living body; an imaging means for detecting the fluorescence produced by the photosensitive substance and forming a fluorescence image of the living body, and an image displaying means for receiving the output from the imaging means and displaying the fluorescence image. In many cases, the fluorescence diagnosing systems take on the forms built in endoscopes to be inserted into the body cavities, operating microscopes, or the like.

Techniques for making a diagnosis of a tumor part without a photosensitive substance being administered to the living body have also been proposed. With the proposed techniques, excitation light, which has wavelengths falling within the excitation wavelength range for an intrinsic dye in the living body, is irradiated to a region of interest in the living body (i.e., the region which is to be used in making a diagnosis). The intrinsic dye in the living body is thus excited by the excitation light and produces fluorescence. By the detection of the fluorescence, the location and infiltration range of the diseased part is displayed as an image, and the displayed image is used in conducting a diagnosis of the tumor part.

Further, a different fluorescence diagnosing system has been proposed in, for example, Japanese Patent Application No. 7(1995)-252295. With the proposed fluorescence diagnosing system, instead of obtaining the two-dimensional image as described above, the intensity of fluorescence produced from each specific point in a region of a living body is detected. A judgment is then made as to whether each point in the region of the living body belongs or does not belong to a tumor part.

However, the above fluorescence diagnosing systems have the problems described below. Specifically, since a region in a living body has protrusions and recesses, the distance between the light source of the excitation light irradiating means and the region of interest in the living body is not uniform. Therefore, the irradiance of the excitation light at each part of the living body, which is exposed to the excitation light, is usually non-uniform. In general, the intensity of fluorescence is approximately in proportion to the irradiance of the excitation light, and the irradiance of the excitation light at a part of the living body exposed to the excitation light is in inverse proportion to the square of the distance between the light source of the excitation light irradiating means and that part of the living body exposed to the excitation light. Accordingly, the problems occur in that a normal part, which is located close to the light source, may produce the fluorescence having a higher intensity than the intensity of the fluorescence produced by a diseased part, which is located remote from the light source. The problems also occur in that the intensity of the fluorescence from a diseased part, which is located at a position inclined with respect to the incident direction of the excitation light, may become markedly low. Thus, if the irradiance of the excitation light is non-uniform, the intensity of the fluorescence will vary in accordance with the level of the irradiance of the excitation light, and therefore an error will often be made in diagnosis of a tumor part.

Therefore, fluorescence diagnosing systems, which are designed such that a change in the intensity of fluorescence due to the non-uniformity of the distance with respect to the region of interest in the living body may be compensated for, have been proposed in, for example, U.S. Pat. No. 4,768,513 and Japanese Patent Publication No.3 (1991)-58729. With the fluorescence diagnosing system proposed in Japanese Patent Publication No. 3(1991)-58729, excitation light is irradiated to a region of a living body, to which a photosensitive substance having a strong affinity for a diseased part has been administered, and the fluorescence produced by the photosensitive substance is detected. Also, the excitation light reflected from that region of the living body is detected. An image operation is then carried out including a division operation between the fluorescence component and the reflected excitation light component by each other. By the division operation, the term due to the distance with respect to the region of interest in the living body is cancelled. However, in the results of the division operation between the fluorescence component and the reflected excitation light component by each other, the term concerning the reflectivity of the portion exposed to the excitation light remains uncancelled. Consequently, the problems remain uneliminated in that a fluorescence image accurately reflecting the distribution of the fluorescent diagnosis drug cannot be obtained.

A different fluorescence imaging technique is proposed in, for example, "Fluorescence Imaging of Early Lung Cancer," Annual International Conference of the IEEE Engineering in Medicine and Biology Society, Vol. 12, No. 3, 1990. With the proposed technique, intrinsic fluorescence, which is produced by an intrinsic dye in an region of interest in a living body when the region of interest is exposed to excitation light, is separated into a fluorescence component corresponding to a green wavelength range (hereinbelow referred to as the "green wavelength component G") and a fluorescence component corresponding to a red wavelength range (hereinbelow referred to as the "red wavelength component R"). An image operation is then carried out including a division operation between the red wavelength component R and the green wavelength component G by each other, and the result of the division operation is displayed. The proposed technique utilizes the findings in that the spectrum of the intrinsic fluorescence produced by a normal part is different from the spectrum of the intrinsic fluorescence produced by a diseased part. Particularly, when the spectrum of the intrinsic fluorescence, which is produced by the intrinsic dye at a normal part in the living body, and the spectrum of the intrinsic fluorescence, which is produced by the intrinsic dye at a diseased part in the living body, are compared with each other, the intensity of the green range of the spectrum obtained from the diseased part is markedly lower than the intensity of the green range of the spectrum obtained from the normal part. Therefore, the degree of reduction in the intensity of the green wavelength component G of the intrinsic fluorescence obtained from the diseased part, as compared with the intensity of the green wavelength component G of the intrinsic fluorescence obtained from the normal part, is markedly higher than the degree of reduction in the intensity of the red wavelength component R of the intrinsic fluorescence obtained from the diseased part, as compared with the intensity of the red wavelength component R of the intrinsic fluorescence obtained from the normal part. Therefore, only the intrinsic fluorescence from the diseased part can be specifically extracted by carrying out the division operation of R/G and can be displayed as a visual image. With the proposed technique, the term of the fluorescence intensity depending upon the distance between the excitation light source (i.e., the excitation light irradiating means) and the region of interest in the living body and the distance between the region of interest in the living body and the fluorescence receiving means can be canceled. However, the proposed technique has the problems in that the signal-to-noise ratio cannot be kept high, since the intensity of the intrinsic fluorescence from the diseased part is markedly low.

Accordingly, a different fluorescence diagnosing technique utilizing the red/green ratio has been proposed in "Fluorescence Image Diagnosis of Cancer Using Red/Green Ratio" by Tokyo Medical College and Hamamatsu Photonics K.K., 16th symposium of The Japanese Society of Laser Medical Science, 1995.

With the proposed technique, the intensity of red fluorescence from a diseased part is amplified by using a fluorescent diagnosis drug, which is capable of accumulating at the diseased part and producing red fluorescence, and an operation of R/G is carried out. As a result, a fluorescence image can be obtained such that the intensity of fluorescence from the diseased part may be kept higher than that with the aforesaid technique proposed in "Fluorescence Imaging of Early Lung Cancer."

In cases where the operation of R/G is carried out as in the two techniques described above, the term of the fluorescence intensity depending upon the distance between the excitation light source and the region of interest in the living body and the distance between the region of interest in the living body and the fluorescence receiving means can be ignored.

However, the intensity of the green intrinsic fluorescence component from the diseased part is markedly low. Therefore, with the two techniques described above, the problems occur in that the division by the value of zero often occurs, and an error readily occurs in making the division operation.

In addition, there has been another problem with those fluorescence diagnosing systems as described above. In conducting the fluorescence diagnosis, multiple images of different wavelength ranges are required for identifying differences between spectral patterns of the normal tissues and diseased tissues. To obtain such multiple images, the fluorescence detecting apparatus in each of the fluorescence diagnosing systems as described above has required use of multiple imaging devices each provided with a color filter of a single color fixed on a detection surface thereof. Such a configuration with the multiple imaging devices undesirably increases the operation cost and the size of the fluorescence detecting apparatus.

SUMMARY OF THE INVENTION

One object of the present invention is to provide a fluorescence detecting apparatus, wherein the fluorescence intensity depending upon the distance between an excitation light source and a region of interest in a living body exposed to excitation light and upon the distance between the region of interest and a fluorescence receiving means is corrected such that no operation error may occur.

Another object of the present invention is to provide a fluorescence detecting apparatus, which enables operation processing realizing a high signal-to-noise ratio to be carried out.

A specific object of the present invention is to provide a fluorescence detecting apparatus, which enables the formation of a fluorescence image, that has good image quality and is capable of serving as an effective tool in the efficient and accurate diagnosis of an illness.

Still another object of the present invention is to provide a fluorescence detecting apparatus with a compact configuration requiring a relatively low operation cost.

The present invention provides a first fluorescence detecting apparatus, wherein excitation light is irradiated to a region of interest in a living body, to which a photosensitive substance (i.e., a fluorescent diagnosis drug) has been administered, and wherein fluorescence, which is produced from the region of interest in the living body when the region of interest is exposed to the excitation light, is detected. Specifically, the present invention provides a first fluorescence detecting apparatus, comprising:

i) an excitation light irradiating means for irradiating excitation light to a region of interest in a living body to which a fluorescent diagnosis drug, that is capable of producing fluorescence when excited with the excitation light has been administered, said excitation light covering wavelengths falling within an excitation wavelength range for said fluorescent diagnosis drug and an intrinsic dye in the living body, said intrinsic dye being capable of producing fluorescence when excited with the excitation light, ii) a fluorescence detecting means for detecting first and second fluorescence components, said first fluorescence component being either one of:

a) an entire fluorescence component covering wavelengths falling within a wavelength range which contains: a wavelength range of extrinsic fluorescence produced by said fluorescent diagnosis drug in said region of interest in the living body, and a wavelength range of intrinsic fluorescence produced by said intrinsic dye in said region of interest in the living body, and b) a fluorescence sum component which is the sum of a fluorescence component covering wavelengths falling within a part of the wavelength range of the extrinsic fluorescence produced by said fluorescent diagnosis drug in said region of interest in the living body, and a fluorescence component covering wavelengths falling within a part of the wavelength range of the intrinsic fluorescence produced by said intrinsic dye in the living body, and said second fluorescence component being either one of:

a) a fluorescence component covering wavelengths falling within a part of the wavelength range of the extrinsic fluorescence, and b) a fluorescence difference component which is the difference between a fluorescence component covering wavelengths falling within a part of the wavelength range of the extrinsic fluorescence, and a fluorescence component covering wavelengths falling within a part of the wavelength range of the intrinsic fluorescence, and iii) a division means for carrying out a division between the first fluorescence component and the second fluorescence component, wherein the fluorescence detecting means comprises:

i) a color mosaic filter for separating the fluorescence emitted from the region of interest into the first fluorescence component and the second fluorescence component, and ii) a detecting means for detecting the first and second fluorescence components in a two-dimensional manner, and wherein the color mosaic filter is fixed on a fluorescence detecting surface of the detecting means.

In the first fluorescence detecting apparatus in accordance with the present invention, it is desirable to employ light covering wavelengths falling within a wavelength range in the vicinity of an excitation peak wavelength for the fluorescent diagnosis drug as the excitation light, such that the signal-to-noise ratio of the fluorescence component detected by each fluorescence detecting means may be enhanced. Alternatively, it is also desirable to employ as the excitation light the light covering wavelengths falling within a wavelength range in the vicinity of the excitation peak wavelength for the fluorescent diagnosis drug and light covering wavelengths falling within a wavelength range in the vicinity of an excitation peak wavelength for the intrinsic dye in the living body.

The term "excitation peak wavelength for a fluorescent diagnosis drug" as used herein means the wavelength of the excitation light, which causes the fluorescent diagnosis drug to produce the extrinsic fluorescence having the highest possible intensity. Also, the term "excitation peak wavelength for an intrinsic dye in a living body" as used herein means the wavelength of the excitation light, which causes the intrinsic dye in the living body to produce the intrinsic fluorescence having the highest possible intensity.

The present invention also provides a second fluorescence detecting apparatus, wherein excitation light is irradiated to a region of interest in a living body, to which no photosensitive substance (i.e., fluorescent diagnosis drug) has been administered, and wherein intrinsic fluorescence, which is produced by an intrinsic dye in the region of interest in the living body when the intrinsic dye is excited with the excitation light, is detected. Specifically, the present invention provides a second fluorescence detecting apparatus, comprising:

i) an excitation light irradiating means for irradiating excitation light to a region of interest in a living body, said excitation light covering wavelengths falling within an excitation wavelength range for an intrinsic dye in the living body, said intrinsic dye being capable of producing fluorescence when excited with the excitation light, ii) a fluorescence detecting means for detecting first and second fluorescence components, said first fluorescence component being either one of:

a) an entire intrinsic fluorescence component covering wavelengths falling within a visible wavelength range, which contains a comparatively short wavelength range and a comparatively long wavelength range among a wavelength range of intrinsic fluorescence produced by said intrinsic dye in said region of interest in the living body, and b) a fluorescence sum component, which is the sum of a fluorescence component covering wavelengths falling within a part of the comparatively short wavelength range among the wavelength range of the intrinsic fluorescence produced by said intrinsic dye in said region of interest in the living body, and a fluorescence component covering wavelengths falling within a part of the comparatively long wavelength range among the wavelength range of the intrinsic fluorescence, and said second fluorescence component being either one of:

a) a fluorescence component covering wavelengths falling within a part of the comparatively long wavelength range among the wavelength range of the intrinsic fluorescence, and b) a fluorescence difference component which is the difference between: a fluorescence component covering wavelengths falling within a part of the comparatively short wavelength range among the wavelength range of the intrinsic fluorescence, and a fluorescence component covering wavelengths falling within a part of the comparatively long wavelength range among the wavelength range of the intrinsic fluorescence, and iii) a division means for carrying out a division operation between the first fluorescence component and the second fluorescence component, wherein the fluorescence detecting means comprises:

i) a color mosaic filter for separating the fluorescence emitted from the region of interest into the first fluorescence component and the second fluorescence component, and ii) a detecting means for detecting the first and second fluorescence components in a two-dimensional manner, and wherein the color mosaic filter is fixed on a fluorescence detecting surface of the detecting means.

In the second fluorescence detecting apparatus in accordance with the present invention, it is desirable to employ light covering wavelengths falling within a wavelength range in the vicinity of an excitation peak wavelength for the intrinsic dye in the living body as the excitation light, such that the signal-to-noise ratio of the fluorescence component detected by each fluorescence detecting means may be enhanced.

The present invention also provides a third fluorescence detecting apparatus comprising:

i) an excitation light irradiating means for irradiating excitation light to a region of interest in a living body, ii) a fluorescence detecting means for detecting at least two fluorescence components of desired wavelength ranges extracted from fluorescence emitted from the region of interest irradiated with the excitation light, and iii) a signal processing means for processing signals representing said at least two fluorescence components detected by the fluorescence detecting means in a predetermined manner, wherein the fluorescence detecting means comprises:

i) a color mosaic filter for separating the fluorescence emitted from the region of interest into said at least two fluorescence components, and ii) a detecting means for detecting said at least two fluorescence components in a two-dimensional manner, and wherein the color mosaic filter is fixed on a fluorescence detecting surface of the detecting means.

The color mosaic filter used in the third fluorescence detecting apparatus may include filter elements of primary colors, or may include filter elements of complementary colors.

In the first and second fluorescence detecting apparatuses in accordance with the present invention, the fluorescence detecting means may detect the fluorescence produced from each of different points in the region of interest. Alternatively, the fluorescence detecting means may carry out two-dimensional detection of the fluorescence (i.e., the extrinsic fluorescence or the intrinsic fluorescence) produced from the region for interest and may thereby obtain a fluorescence image of the region of interest.

With the first and second fluorescence detecting apparatuses in accordance with the present invention, wherein the entire fluorescence component covering the wavelengths falling within the predetermined wavelength range or the fluorescence sum component, which is the sum of the fluorescence components each covering wavelengths falling within the desired wavelength range, is employed as the denominator in the division, the value of the denominator in the division can be kept sufficiently large. Therefore, the problem of an operation error due to division by the value of zero can be prevented. Also, the adverse effects from fluctuation in the intensity of fluorescence, due to the distance between the excitation light irradiating means and the region of interest in the living body and the distance between the region of interest in the living body and the fluorescence receiving means, can be eliminated reliably.

Further, in cases where light covering wavelengths falling within a wavelength range in the vicinity of the excitation peak wavelength for the fluorescent diagnosis drug and/or covering wavelengths falling within a wavelength range in the vicinity of the excitation peak wavelength for the intrinsic dye in the living body is employed as the excitation light, the values of both the denominator and the numerator in the division can be kept sufficiently large. Therefore, operation processing realizing a high signal-to-noise ratio can be carried out.

The first and second fluorescence detecting apparatuses in accordance with the present invention may be applied to a fluorescence diagnosing system, wherein a fluorescence image is formed using an imaging means, such as an image sensor, as the fluorescence detecting means. In such cases, a fluorescence image can be obtained, in which the adverse effects from fluctuation in the intensity of fluorescence due to the aforesaid distances have been eliminated. Also, a fluorescence image having good image quality with a high signal-to-noise ratio can be obtained. Therefore, a fluorescence image can be obtained, which has good image quality and is capable of serving as an effective tool in the efficient and accurate diagnosis of an illness.

In either of the first, second or third fluorescence detecting apparatus in accordance with the present invention, the color mosaic filter separates the fluorescence emitted from the region of interest into a plurality of fluorescence components of desired wavelength ranges. Accordingly, the configuration of the fluorescence detecting means can be simplified. In addition, at least two fluorescence components of desired wavelength ranges can be detected using a single detecting means, providing a fluorescence detecting apparatus with a compact configuration requiring a relatively low operation cost.

In the case where the color mosaic filter includes the filter elements of primary colors, each fluorescence component can be extracted and detected requiring only simple signal processing.

In the case where the color mosaic filter includes the filter elements of complementary colors, each fluorescence component of a desired wavelength range can be derived from the fluorescence components of wavelength ranges corresponding to the complementary colors, i.e., the fluorescence emitted by the region of interest is used with higher efficiency. Accordingly, the S/N ratio of each fluorescence component can be improved as effects of noises are restrained.

BRIEF DESCRIPTION OF THE DRAWINGS

FIG. 7 is a schematic view of a color mosaic filter fixed on a detection surface of a high-sensitivity camera unit used in the first embodiment, FIG. 8 shows optical transmission characteristics of individual filter elements constituting the color mosaic filter shown in FIG. 7, FIG. 9 is a graph showing an example of an excitation light spectrum of excitation light emitted by an excitation light source in the first embodiment, FIG. 13 illustrates a color mosaic filter used in the endoscope system shown in FIG. 12.

DESCRIPTION OF THE PREFERRED EMBODIMENTS

Figure 1:
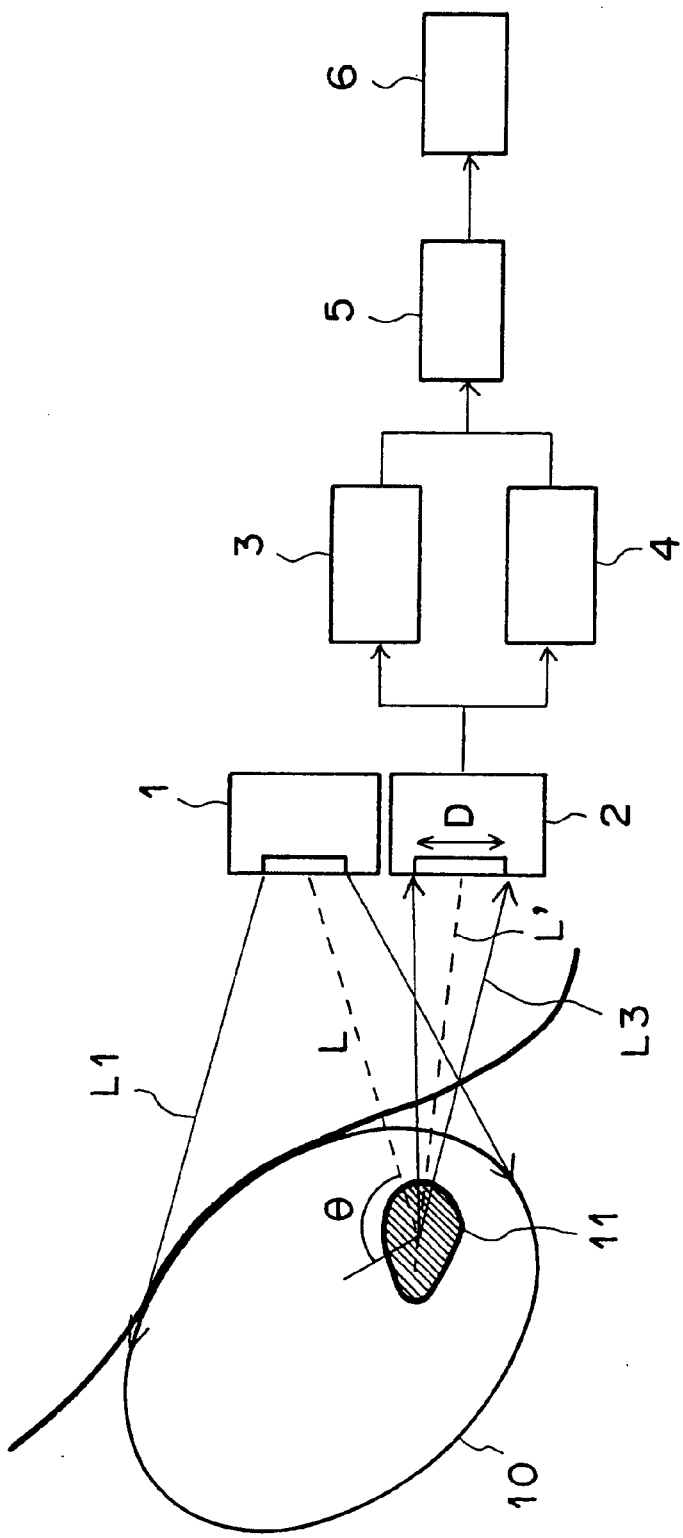
FIG. 1 is an explanatory view showing a fundamental structure of a fluorescence detecting apparatus in accordance with the present invention.

The present invention will hereinbelow be described in further detail with reference to the accompanying drawings. FIG. 1 shows a fundamental structure of a fluorescence detecting apparatus in accordance with the present invention.

As the fundamental structure, the fluorescence detecting apparatus comprises an excitation light irradiating means 1 for irradiating excitation light L1 to a region of interest 10 in a living body, and a fluorescence receiving optical system 2 for receiving fluorescence L3, which is produced from the region of interest 10 in the living body. The fluorescence detecting apparatus also comprises a fluorescence detecting means 3 for separating the fluorescence L3 into fluorescence components, each covering wavelengths falling within a desired wavelength range, and detecting the fluorescence component or a fluorescence difference component, which is the difference between fluorescence components each covering wavelengths falling within desired wavelength range.

The fluorescence detecting apparatus further comprises another fluorescence detecting means 4 for detecting: an entire fluorescence component covering wavelengths falling within a predetermined wavelength range among the wavelength range of the fluorescence L3; or a fluorescence sum component, which is the sum of fluorescence components each covering wavelengths falling within a desired wavelength range. The fluorescence detecting apparatus still further comprises a division means 5 for carrying out a division operation using the outputs obtained from the fluorescence detecting means 3 and the fluorescence detecting means 4. By way of example, the output obtained from the division means 5 is fed as image information into a display means 6 for displaying a visible image. Each of the fluorescence detecting means 3 and the fluorescence detecting means 4 may be constituted as a fluorescence detecting means incorporating the fluorescence receiving optical system 2. In FIG. 1, as an aid in facilitating the explanation, the fluorescence receiving optical system 2 is illustrated as being separated from the fluorescence detecting means 3 and the fluorescence detecting means 4.

Described hereinbelow is how the intensity of fluorescence, which depends upon the distance between the excitation light irradiating means 1 and the region of interest in the living body exposed to the excitation light and upon the distance between the region of interest 10 in the living body and the fluorescence receiving optical system 2, is corrected in the fluorescence detecting apparatus having the fundamental structure described above.

With the fluorescence detecting apparatus, the excitation light may be irradiated to the region of interest in the living body, to which the photosensitive substance (i.e., the fluorescent diagnosis drug) has been administered. Then, the extrinsic fluorescence, which is produced by the fluorescent diagnosis drug when the region of interest in the living body is exposed to the excitation light, and the intrinsic fluorescence, which is produced by an intrinsic dye in the region of interest in the living body when the region of interest is exposed to the excitation light, are detected. (Such cases will hereinbelow be referred to as "cases where the fluorescence with the administration of the drug is detected.") In this case, an extrinsic fluorescence component Ex and a fluorescence sum component (Ex+In), which is the sum of the extrinsic fluorescence component Ex and an intrinsic fluorescence component In, are divided by each other. The structure of the apparatus for such a case will hereinbelow be described in detail.

The excitation light having a wavelength $\lambda_{ex}$ is produced by the excitation light irradiating means 1 and irradiated to the region of interest 10 in the living body, to which the fluorescent diagnosis drug has been administered and which contains a diseased part 11. When the region of interest 10 in the living body is exposed to the excitation light, the region of interest 10 is excited and produces the fluorescence L3. The fluorescence L3 is received by the fluorescence receiving optical system 2. The fluorescence L3 is separated with respect to wavelength ranges by a dichroic mirror, an optical filter, or the like. The extrinsic fluorescence component, which is produced by the fluorescent diagnosis drug in the region of interest 10 in the living body, and the fluorescence sum component, which is the sum of the extrinsic fluorescence component and the intrinsic fluorescence component produced by the intrinsic dye in the region of interest 10 in the living body, are thereby separated from each other. The fluorescence detecting means 3 detects the extrinsic fluorescence component, and the fluorescence detecting means 4 detects the fluorescence sum component. The photo-detecting device employed in each of the fluorescence detecting means 3 and the fluorescence detecting means 4 may be a photo-detecting device, such as a photodiode, which detects the fluorescence L3 for each of different points in the region of interest 10 in the living body. Alternatively, the photo-detecting device may be a charge coupled device image sensor, or the like, which two-dimensionally detects the fluorescence L3 and forms a fluorescence image. This also applies to other possible structures, which will be described later.

The wavelength range of the extrinsic fluorescence component, which is detected by the fluorescence detecting means 3, and the wavelength range of the extrinsic fluorescence component, which is contained in the fluorescence sum component detected by the fluorescence detecting means 4, need not necessarily be identical with each other. Also, the means for detecting the extrinsic fluorescence component and the means for detecting the fluorescence sum component are not limited to those employed in this structure, As an alternative, fluorescence components each covering wavelengths falling within a predetermined wavelength range may be separated from each other and detected, so that a fluorescence component covering wavelengths falling within a wavelength range to be used ultimately may be calculated by carrying out an operation, such as addition or subtraction, on the results of the detection. For example, the fluorescence L3 may be separated with respect to wavelength ranges, and the extrinsic fluorescence component and the intrinsic fluorescence component may thereby be separated from each other. Thereafter, the extrinsic fluorescence component may be detected by the fluorescence detecting means 3, and the intrinsic fluorescence component may be detected by the fluorescence detecting means 4. The outputs obtained from the fluorescence detecting means 3 and the fluorescence detecting means 4 may then be added to each other, and the fluorescence sum component may thereby be 15;, obtained. As another alternative, the fluorescence L3 may be separated with respect to wavelength ranges, and the intrinsic fluorescence component and the fluorescence sum component, which is the sum of the extrinsic fluorescence component and the intrinsic fluorescence component, may thereby be separated from each other. Also, the intrinsic fluorescence component may be detected by the fluorescence detecting means 3, and the fluorescence sum component may be detected by the fluorescence detecting means 4. Thereafter, the intrinsic fluorescence component may be subtracted from the fluorescence sum component, so that the extrinsic fluorescence component may thereby be obtained.

Figure 2:
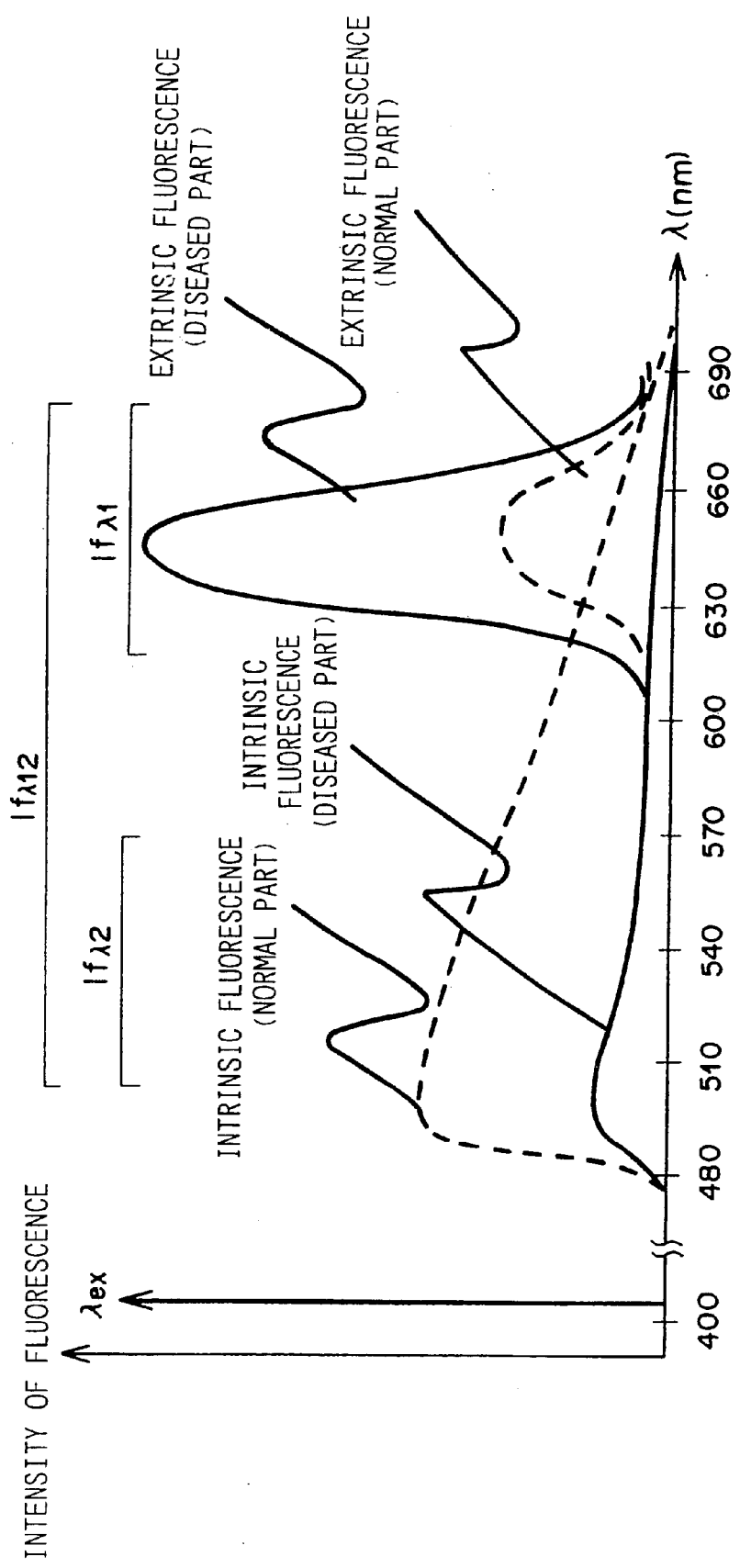
FIG. 2 is a graph showing the relationship among wavelength $\lambda_{ex}$ of excitation light, an intrinsic fluorescence component If$\lambda_2$, and an extrinsic fluorescence component If$\lambda_1$.

How the fluorescence detecting apparatus having the structure described above operates will be described hereinbelow. When the excitation light L1 is irradiated to the region of interest in the living body, the region of interest 10 in the living body is excited by the excitation light L1 and produces the fluorescence L3 having a spectrum as illustrated in FIG. 2. The fluorescence L3 comprises an intrinsic fluorescence component If$\lambda_2$, which is produced in the living body by the intrinsic dye, such as FAD or NADH, and an extrinsic fluorescence component If $\lambda_1$, which is produced by the fluorescent diagnosis drug having been accumulated at a diseased part. Ordinarily, the intrinsic fluorescence component If$\lambda_2$ has the maximum peak in the vicinity of a wavelength of 500 nm and attenuates markedly in the region longer than a wavelength of 600 nm. The extrinsic fluorescence component If$\lambda_1$ has the maximum peak at a wavelength longer than 600 nm.

The wavelength components detected by the fluorescence detecting means 3 and the fluorescence detecting means 4 may be represented as described below.

The extrinsic fluorescence component If$\lambda_1$ may be represented by the formula shown below.

$$If\lambda_1 = k\lambda_1 \cdot I\lambda_{ex} \cdot \eta F\lambda_1 \cdot N \cdot \eta D$$

The apparent intrinsic fluorescence component If$\lambda_2$ may be represented by the formula shown below.

$$If\lambda_2 = k\lambda_2 \cdot I\lambda_{ex} \cdot \eta F\lambda_2 \cdot N \cdot \eta D$$

The fluorescence sum component If$\lambda_+$ maybe represented by the formula shown below.

$$If\lambda_+ = If\lambda_1 + If\lambda_2$$

Unless otherwise specified, the symbols used herein for the cases where the fluorescence with the administration of the drug is detected have the meanings described below. This also applies to the below-described cases where the fluorescence with the administration of the drug is detected.

$\lambda_{ex}$: The wavelength of the excitation light.

I$\lambda_{ex}$: The intensity of the excitation light at the region of interest in the living body; wherein the intensity depends upon the distance L between the excitation light source (i.e., the excitation light irradiating means) and the region of interest in the living body, the power P of the excitation light source, and the angle θ made between the excitation light beam and the region of interest in the living body. That is, I$\lambda_{ex}$=I$\lambda_{ex}$(L, P, θ).

n: The concentration of the apparent intrinsic fluorescent molecules. (It is considered that a plurality of kinds of intrinsic fluorescent molecules are present in the living body. They can virtually be processed such that only a single kind of molecules may be present, and therefore the term "apparent" is used herein.)

N: The concentration of the extrinsic fluorescent molecules.

k$\lambda_1$: A constant, which depends upon the wavelength $\lambda_{ex}$ of the excitation light and the extrinsic fluorescent molecules.

k$\lambda_2$: A constant, which depends upon the wavelength $\lambda_{ex}$ Of the excitation light and the apparent intrinsic fluorescent molecules.

k$\lambda_{12}$: A constant, which depends upon the wavelength $\lambda_{ex}$ of the excitation light and the apparent fluorescent molecules contributing to the fluorescence covering wavelengths falling within the entire wavelength range.

$\eta F\lambda_1$: The fluorescence quantum yield of the extrinsic fluorescent molecules with respect to the wavelength $\lambda_{ex}$ of the excitation light.

$\eta F\lambda_2$: The fluorescence quantum yield of the apparent intrinsic fluorescent molecules with respect to the wavelength $\lambda_{ex}$ of the excitation light.

$\eta F\lambda_{12}$: The fluorescence quantum yield of the apparent fluorescent molecules contributing to the fluorescence covering wavelengths falling within the entire wavelength range, with respect to the wavelength $\lambda_{ex}$ of the excitation light.

$\eta D$: The fluorescence detection efficiency, which depends upon the distance L' between the region of interest and the fluorescence receiving optical system, the size D of the aperture of the fluorescence receiving optical system, and the efficiency ξ of the photo detecting device. That is, $\eta D = \eta D(L', \xi, D)$. (In the strict sense, the detection efficiency with respect to the intrinsic fluorescence and the detection efficiency with respect to the extrinsic fluorescence are different from each other. However, they can herein be processed as being approximately equal to each other.)

Thereafter, the division means 5 carries out the division operation of the extrinsic fluorescence component If $\lambda_1$ by the fluorescence sum component If$\lambda_+$. The division may be represented by the formula shown below.

$$\text{If } \lambda_1 / \text{If } \lambda_+ = (k\lambda_1 \cdot \eta F\lambda_1 \cdot N)/(k\lambda_1 \cdot \eta F\lambda_1 \cdot N + k\lambda_2 \cdot \eta F\lambda_2 \cdot n)$$

If $(k\lambda_1 \cdot \eta F\lambda_1)/(k\lambda_2 \cdot \eta F\lambda_2) = C$ and $N/n = X$, the formula shown below will obtain.

$$\text{If}\lambda_1 / \text{If}\lambda_+ = (C \cdot X)/(C \cdot X + 1)$$

Figure 3:
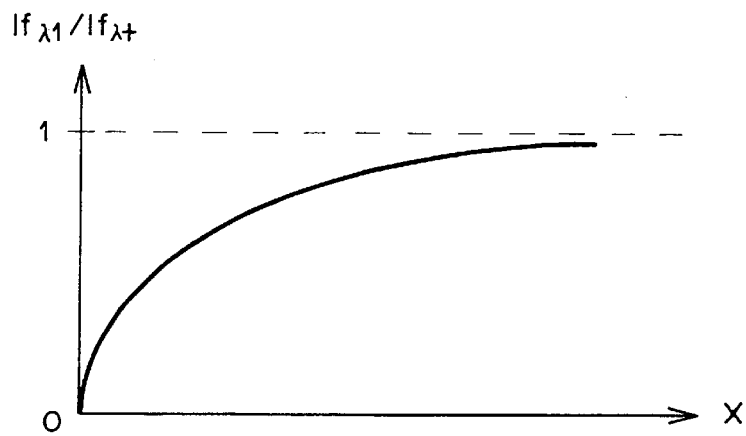
FIG. 3 is a graph showing the relationship between a quotient If$\lambda_1$/If$\lambda$+, which is obtained by dividing an extrinsic fluorescence component If$\lambda_1$ by a fluorescence sum component If $\lambda_+$, and a variable N/n=X, which represents the concentration of an extrinsic fluorescent molecules having been normalized with the concentration of an intrinsic fluorescent molecules.

Since C is a constant term, If$\lambda_1$/If$\lambda_+$ follows the curve shown in FIG. 3. Specifically, the non-uniformity I$\lambda_{ex}$ of the irradiance of the excitation light, depending upon sites, is canceled. The value of X represents the concentration of the extrinsic fluorescent molecules having been normalized with the concentration of the intrinsic fluorescent molecules. A large value of If$\lambda_1$/If$\lambda_+$ indicates that the region of interest is located at a diseased part. In this manner, the diseased part can be detected specifically by carrying out the division operation of the extrinsic fluorescence component If$\lambda_1$ by the fluorescence sum component If$\lambda_+$. In cases where the fluorescence sum component If$\lambda_+$ is used as the denominator in the division operation, the value of the denominator can be kept large, and therefore the occurrence of an operation error due to division by the value of zero can be restrained. Accordingly, for example, if an image sensor is employed as each of the fluorescence detecting means 3 and the fluorescence detecting means 4, a fluorescence image, in which the intensity of fluorescence has been corrected, can be displayed as a visible image on the display means 6.

Figure 4:
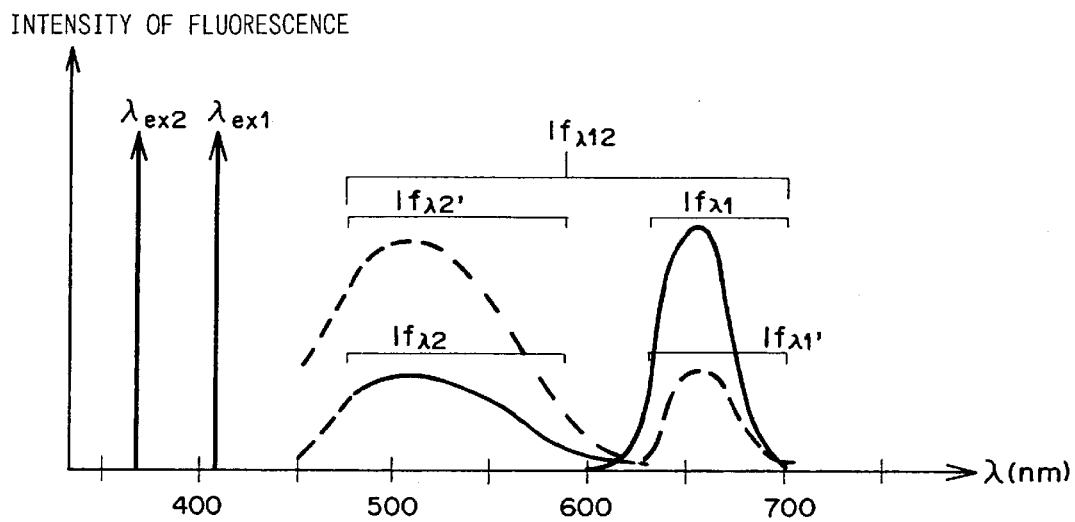
FIG. 4 is a graph showing the relationship between an intrinsic fluorescence component If$\lambda_2$, If$\lambda_2'$ and an extrinsic fluorescence component If$\lambda_1$, If$\lambda_1'$, which are obtained when light, that covers wavelengths falling within a wavelength range in the vicinity of an excitation peak wavelength $\lambda_{ex}$, for a fluorescent diagnosis drug, and light, that covers wavelengths falling within a wavelength range in the vicinity of an excitation peak wavelength $\lambda ex_2$ for an intrinsic dye in a living body, are employed as excitation light.

As an alternative to the excitation light described above, light covering wavelengths falling within a wavelength range in the vicinity of an excitation peak wavelength $\lambda_{ex1}$ for the fluorescent diagnosis drug or light covering wavelengths falling within a wavelength range in the vicinity of an excitation peak wavelength $\lambda_{ex2}$ for the intrinsic dye in the living body may be employed as the excitation light. In such cases, the fluorescence having the spectrum illustrated in FIG. 4 can be obtained from the region of interest 10 in the living body. The symbols used herein for such cases have the meanings described below.

If$\lambda_1$: The contribution of the excitation light, which has a wavelength of $\lambda_{ex1}$, to the extrinsic fluorescence among the fluorescence produced from the region of interest in the living body.

If$\lambda_1$': The contribution of the excitation light, which has a wavelength of $\lambda_{ex2}$, to the extrinsic fluorescence among the fluorescence produced from the region of interest in the living body.

If$\lambda_2$: The contribution of the excitation light, which has a wavelength of $\lambda_{ex1}$ to the intrinsic fluorescence among the fluorescence produced from the region of interest in the living body.

If$\lambda_{ex1}$: The contribution of the excitation light, which has a wavelength of $\lambda_{ex2}$, to the intrinsic fluorescence among the fluorescence produced from the region of interest in the living body.

I$\lambda_{ex1}$: The intensity of the excitation light, which has a wavelength of $\lambda_{ex1}$, at the region of interest in the living body.

I$\lambda_{ex2}$: The intensity of the excitation light, which has a wavelength of $\lambda_{ex2}$, at the region of interest in the living body. Also, in such cases, it is assumed that I$\lambda_{ex1}$ and I$\lambda_{ex2}$ have the same distribution of light, and that I$\lambda_{ex2} = m \cdot \text{I}\lambda_{ex1}$ (where m is an arbitrary constant) at the region of interest in the living body.

In the same manner as that described above, fluorescence components each covering wavelengths falling within a predetermined wavelength range are separated from each other. The extrinsic fluorescence component If$\lambda_1$+If$\lambda_1$' is detected by the fluorescence detecting means 3, and the fluorescence sum component If$\lambda_+$=If$\lambda_1$+If$\lambda_1$'+If$\lambda_2$+If$\lambda_2$' is detected by the fluorescence detecting means 4.

In such cases, If$\lambda_1$, If$\lambda_1$', If$\lambda_2$, and If$\lambda_2$' are represented by the formulae shown below.

$$\text{If}\lambda_1 = k_1\lambda_1 \cdot \text{I}\lambda_{ex1} \cdot \eta F\lambda_1 \cdot N \cdot \eta D$$

$$\text{If}\lambda_1' = k_1\lambda_1' \cdot \text{I}\lambda_{ex1} \cdot \eta F\lambda_1' \cdot N \cdot \eta D$$

$$\text{If}\lambda_2 = k_2\lambda_2 \cdot \text{I}\lambda_{ex2} \cdot \eta F\lambda_2 \cdot N \cdot \eta D$$

$$\text{If}\lambda_2' = k_2\lambda_2' \cdot \text{I}\lambda_{ex2} \cdot \eta F\lambda_2' \cdot N \cdot \eta D$$

The symbols used herein for such cases have the meanings described below.

$k_1\lambda_1$: A constant, which depends upon the wavelength $\lambda_{ex1}$ of the excitation light and the extrinsic fluorescent molecules.

$k_1\lambda_1$': A constant, which depends upon the wavelength $\lambda_{ex2}$ of the excitation light and the extrinsic fluorescent molecules.

$\eta F\lambda_1$: The fluorescence quantum yield of the extrinsic fluorescent molecules with respect to the wavelength $\lambda_{ex1}$ of the excitation light.

$\eta F\lambda_1$': The fluorescence quantum yield of the extrinsic fluorescent molecules with respect to the wavelength $\lambda_{ex2}$ of the excitation light.

$k_2\lambda_2$: A constant, which depends upon the wavelength $\lambda_{ex1}$ of the excitation light and the intrinsic fluorescent molecules.

$k_2\lambda_2$': A constant, which depends upon the wavelength $\lambda_{ex2}$ of the excitation light and the intrinsic fluorescent molecules.

$\eta F\lambda_2$: The fluorescence quantum yield of the apparent intrinsic fluorescent molecules with respect to the wavelength $\lambda_{ex1}$ of the excitation light.

$\eta F\lambda_2$': The fluorescence quantum yield of the apparent intrinsic fluorescent molecules with respect to the wavelength $\lambda_{ex2}$ of the excitation light.

Thereafter, the division means 5 carries out the division operation of the extrinsic fluorescence component If $\lambda_1$+If$\lambda_1$' by the fluorescence sum component If$\lambda_+$=If$\lambda_1$+If$\lambda_1$'+If$\lambda_2$+If$\lambda_2$'. The division operation is represented by the formula shown below.

$$(\text{If } \lambda_1 + \text{If } \lambda_1')/(\text{If } \lambda_1 + \text{If } \lambda_1' + \text{If } \lambda_2 + \text{If } \lambda_2') = C \cdot X(1 + C \cdot X)$$

where $$C = (k_1\lambda_1 \cdot \eta F\lambda_1 + k_1\lambda_1' \cdot m \cdot \eta F\lambda_1')/(k_2\lambda_2 \cdot \eta F\lambda_2 + k_2\lambda_2' \cdot m \cdot \eta F\lambda_2')$$

$X = N/n$

Figure 5:
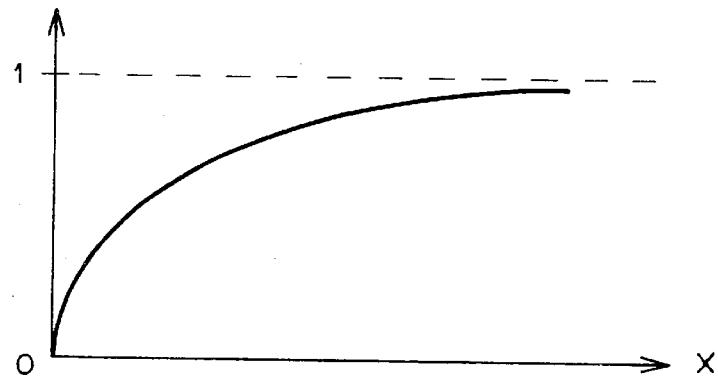
FIG. 5 is a graph showing the relationship between a quotient $If\lambda_1/If\lambda_+ = (If\lambda_1 + If\lambda_1')/(If\lambda_1 + If\lambda_1' + If\lambda_2 + If\lambda_2')$ which is obtained by dividing an extrinsic fluorescence component $If\lambda_1$ by a fluorescence sum component $If\lambda_+$, and a variable $N/n = X$, which represents the concentration of an extrinsic fluorescent molecules having been normalized with the concentration of an intrinsic fluorescent molecules.

Since C is a constant term, (If$\lambda_+$If$\lambda_1$')/If$\lambda_1$+If$\lambda_1$'+If$\lambda_2$+If$\lambda_2$') follows the curve shown in FIG. 5. Specifically, the non-uniformity I$\lambda_{ex1}$ and the non-uniformity I$\lambda_{ex2}$ of the irradiance of the excitation light, depending upon sites, are canceled. The value of X represents the concentration of the extrinsic fluorescent molecules having been normalized with the concentration of the intrinsic fluorescent molecules. A large value of $(If\lambda_1 + If\lambda_1')/(If\lambda_1 + If\lambda_1' + If\lambda_2 + If\lambda_2')$ indicates that the region of interest is located at a diseased part.

Therefore, in such cases, the fluorescence produced from the diseased part can be specifically detected as an image by carrying out the division operation of the fluorescence image, which is obtained in accordance with the extrinsic fluorescence component If $\lambda_1 + If\lambda_1'$, by the fluorescence image, which is obtained in accordance with the fluorescence sum component $If\lambda_+$. In this manner, the diseased part can be detected specifically by carrying out the division operation of the extrinsic fluorescence component $If\lambda_1 + If\lambda_1'$ by the fluorescence sum component $If\lambda_+$. In cases where the fluorescence sum component $If\lambda_+$ is used as the denominator in the division operation, the value of the denominator can be kept large, and therefore the occurrence of an operation error due to division by the value of zero can be restrained. Accordingly, for example, if an image sensor is employed as each of the fluorescence detecting means 3 and the fluorescence detecting means 4, a fluorescence image, in which the intensity of fluorescence has been corrected, can be displayed as a visible image on the display means 6. Also, in cases where the light, which covers wavelengths falling within a wavelength range in the vicinity of an excitation peak wavelength $\lambda_{ex1}$ for the fluorescent diagnosis drug, or the light, which covers wavelengths falling within a wavelength range in the vicinity of an excitation peak wavelength $\lambda_{ex2}$ for the intrinsic dye in the living body, are thus employed as the excitation light, the intensity of fluorescence can be kept sufficiently high, and a fluorescence image having good image quality with a high signal-to-noise ratio can be obtained.

The structure described above is designed for the cases where the fluorescence with the administration of the drug is detected, and the extrinsic fluorescence component is divided by the fluorescence sum component, which is the sum of the extrinsic fluorescence component and the intrinsic fluorescence component. A structure described below is designed for the fluorescence detecting apparatus, wherein the intrinsic fluorescence produced from the region of interest in the living body, to which no fluorescent diagnosis drug has been administered, is detected. (Such cases will hereinbelow be referred to as "cases where the autofluorescence without the administration of the drug is detected.") In such cases, the excitation light is irradiated to the region of interest in the living body, to which no fluorescent diagnosis drug has been administered. When the region of interest in the living body is exposed to the excitation light, the intrinsic fluorescence is produced by the intrinsic dye in the region of interest in the living body. A fluorescence component (for example, a red wavelength component R: hereinbelow referred to as the "long wavelength component"), which covers wavelengths falling within a comparatively long wavelength range among the wavelength range of the intrinsic fluorescence having been produced by the intrinsic dye in the living body, is extracted from the intrinsic fluorescence. Also, a fluorescence sum component, which is the sum of the long wavelength component and a fluorescence component (for example, a green wavelength component G: hereinbelow referred to as the "short wavelength component"), which covers wavelengths falling within a comparatively short wavelength range among the wavelength range of the intrinsic fluorescence having been produced by the intrinsic dye in the living body, is detected. The long wavelength component is then divided by the fluorescence sum component. The structure of the apparatus for such a case will hereinbelow be described in detail.

In this structure, as in the aforesaid cases where the fluorescence with the administration of the drug is detected, the intrinsic fluorescence L3, which is produced by the intrinsic dye in the region of interest 10 in the living body, is separated with respect to wavelength ranges by a dichroic mirror, an optical filter, or the like. The long wavelength component $If\lambda_1$ and a fluorescence sum component $If\lambda_+$, which is the sum of the long wavelength component $If\lambda 1$ and the short wavelength component If $\lambda_2$, are thereby separated from each other. The fluorescence detecting means 3 detects the long wavelength component among the intrinsic fluorescence L3 produced by the intrinsic dye in the region of interest 10 in the living body. The fluorescence detecting means 4 detects the fluorescence sum component among the intrinsic fluorescence L3 produced by the intrinsic dye in the region of interest 10 in the living body. The other features are the same as those in the aforesaid cases where the fluorescence with the administration of the drug is detected. The means for detecting the long wavelength component and the means for detecting the fluorescence sum component are not limited to those employed in this structure. As an alternative, fluorescence components each covering wavelengths falling within a predetermined wavelength range may be separated from each other and detected, so that a fluorescence component covering wavelengths falling within a wavelength range to be used ultimately may be calculated by carrying out an operation, such as addition or subtraction, on the results of the detection. For example, the fluorescence L3 may be separated with respect to wavelength ranges, and the long wavelength component and the short wavelength component may thereby be separated from each other. Thereafter, the long wavelength component may be detected by the fluorescence detecting means 3, and the short wavelength component may be detected by the fluorescence detecting means 4. The outputs obtained from the fluorescence detecting means 3 and the fluorescence detecting means 4 may then be added to each other, so that the fluorescence sum component may thereby be obtained. As another alternative, the fluorescence L3 may be separated with respect to wavelength ranges, and the short wavelength component and the fluorescence sum component, which is the sum of the long wavelength component and the short wavelength component, may thereby be separated from each other. Also, the short wavelength component may be detected by the fluorescence detecting means 3, and the fluorescence sum component may be detected by the fluorescence detecting means 4. Thereafter, the short wavelength component may be subtracted from the fluorescence sum component, so that the long wavelength component may thereby be obtained.

How the fluorescence detecting apparatus having this structure operates will be described hereinbelow. When the excitation light L1 is irradiated to the region of interest 10 in the living body, the region of interest 10 in the living body is excited by the excitation light L1 and produces the intrinsic fluorescence L3 having a spectrum illustrated in FIG. 11. It is assumed that the intrinsic fluorescence L3 comprises the fluorescence produced by various kinds of intrinsic dyes in the living body, such as FAD, collagen, fibronectin, and porphyrin.

Figure 11:
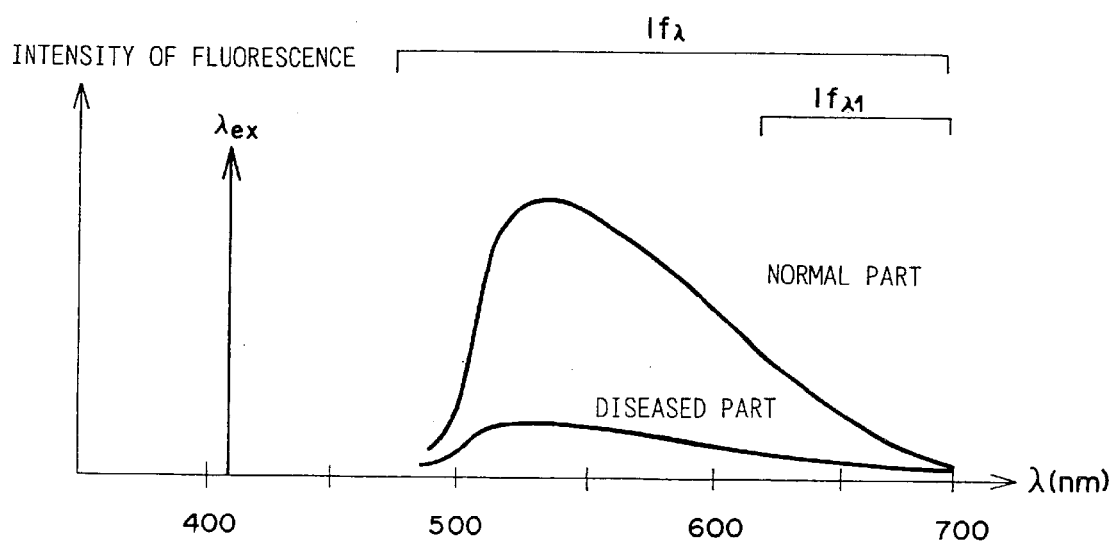
FIG. 11 is a graph showing an example of an autofluorescence spectrum.

As illustrated in FIG. 11, the level and the pattern of the spectrum of the fluorescence vary for the normal part and the diseased part. The level of the intrinsic fluorescence L3 produced from the normal part is high as a whole, and the level of the intrinsic fluorescence L3 produced from the diseased part is low as a whole. Also, in particular, as for the intrinsic fluorescence L3, which is obtained from the diseased part, the degree of reduction in the level of the fluorescence component covering wavelengths longer than the wavelengths of the red color, as compared with the level of the fluorescence component which is of the intrinsic fluorescence L3 obtained from the normal part and which covers wavelengths longer than the wavelength of the red color, is smaller than the degree of reduction in the level of the fluorescence component of the blue to green range, as compared with the level of the fluorescence component which is of the blue to green range in the intrinsic fluorescence L3 obtained from the normal part. (The reason why the fluorescence spectrum varies for the diseased part and the normal part has not yet been clarified completely.) Specifically, the ratio of the fluorescence component in the vicinity of the red color (i.e., the long wavelength component) If$\lambda_1$ to the fluorescence component in the vicinity of the green color (i.e., the short wavelength component) If$\lambda_2$ varies for the diseased part and the normal part. Therefore, it can be judged that a site associated with a large value of quotient If$\lambda_1$/If$\lambda_2$ is the one belonging to the diseased part, and that a site associated with a small value of quotient If$\lambda_1$/If$\lambda_2$ is the one belonging to the normal part. The respective wavelength components may be represented as described below.

The apparent long wavelength component If$\lambda_1$, which is obtained when the excitation light L1 is irradiated to the region of interest 10 in the living body, may be represented by the formula shown below.

$$If\lambda_1 = k\lambda_1 \cdot I\lambda_{ex} \cdot \eta F\lambda_1 \cdot n \cdot \eta D$$

The apparent short wavelength component If$\lambda_2$, which is obtained when the excitation light L1 is irradiated to the region of interest 10 in the living body, may be represented by the formula shown below.

$$If\lambda_2 = k\lambda_2 \cdot I\lambda_{ex} \cdot \eta F\lambda_2 \cdot N \cdot \eta D$$

Therefore, the fluorescence sum component If$\lambda_+$, which is the sum of the long wavelength component and the short wavelength component, may be represented by the formula shown below.

$$If\ \lambda_+ = (k\lambda_1 \cdot I\lambda_{ex} \cdot \eta F\lambda_1 \cdot n \cdot \eta D) + (k\lambda_2 \cdot I\lambda_{ex} \cdot \eta F\lambda_2 \cdot N \cdot \eta D)$$

Unless otherwise specified, the symbols used herein for the cases where the autofluorescence without the administration of the drug is detected have the meanings described below. This also applies to the below-described cases where the autofluorescence without the administration of the drug is detected.

$\lambda_{ex}$: The wavelength of the excitation light.

I$\lambda_{ex}$: The intensity of the excitation light at the region of interest in the living body; wherein intensity depends upon the distance L between the excitation light source (i.e., the excitation light irradiating means) and the region of interest in the living body, the power P of the excitation light source, and the angle θ made between the excitation light beam and the region of interest in the living body. That is, I$\lambda_{ex}$=I$\lambda_{ex}$(L, P, θ).

n: The concentration of the apparent intrinsic fluorescent molecules, which contribute to the fluorescence covering wavelengths falling within the long wavelength range. (It is considered that a plurality of kinds of fluorescent molecules contributing to the intrinsic fluorescence are present in the living body. They can virtually be processed such that only a single kind of molecules may be present, and therefore the term "apparent" is used herein.)

N: The concentration of the apparent intrinsic fluorescent molecules, which contribute to the fluorescence covering wavelengths falling within the short wavelength range.

M: The concentration of the apparent intrinsic fluorescent molecules, which contribute to the fluorescence covering wavelengths falling within the entire wavelength range.

k$\lambda_1$: A constant, which depends upon the wavelength $\lambda_{ex}$ of the excitation light and the apparent intrinsic fluorescent molecules, which contribute to the fluorescence covering wavelengths falling within the long wavelength range.

k$\lambda_2$: A constant, which depends upon the wavelength $\lambda_{ex}$ of the excitation light and the apparent intrinsic fluorescent molecules, which contribute to the fluorescence covering wavelengths falling within the short wavelength range.

k$\lambda_{12}$: A constant, which depends upon the wavelength $\lambda_{ex}$ of the excitation light and the apparent intrinsic fluorescent molecules, that contribute to the fluorescence covering wavelengths falling within the entire wavelength range.

ηF$\lambda_1$: The fluorescence quantum yield of the apparent intrinsic fluorescent molecules, which contribute to the fluorescence covering wavelengths falling within the long wavelength range, with respect to the wavelength $\lambda_{ex}$ of the excitation light.

ηF$\lambda_2$: The fluorescence quantum yield of the apparent intrinsic fluorescent molecules, which contribute to the fluorescence covering wavelengths falling within the short wavelength range, with respect to the wavelength $\lambda_{ex}$ of the excitation light.

ηF$\lambda_{12}$: The fluorescence quantum yield of the apparent intrinsic fluorescent molecules, which contribute to the fluorescence covering wavelengths falling within the entire wavelength range, with respect to the wavelength $\lambda_{ex}$ of the excitation light.

ηD: The fluorescence detection efficiency, which depends upon the distance L' between the region of interest and the fluorescence receiving optical system, the size D of the aperture of the fluorescence receiving optical system, and the efficiency ξ of the photo detecting device. That is, ηD=ηD(L', ε, D). (In the strict sense, the detection efficiency with respect to the fluorescence, which covers wavelengths falling within the short wavelength range, and the detection efficiency with respect to the fluorescence, which covers wavelengths falling within the long wavelength range, are different from each other. However, they can herein be processed as being approximately equal to each other.)

Thereafter, the division means 5 carries out the division operation of the long wavelength component If$\lambda_1$ by the fluorescence sum component If$\lambda_+$(=If$\lambda_1$+If$\lambda_2$). The quotient of the division If$\lambda_1$/(If$\lambda_1$+If$\lambda_2$) may be represented by the formula shown below.

$$If\ \lambda_1 / (If\ \lambda_1 + If\ \lambda_2) = (k\lambda_1 \cdot \eta F\lambda_1 \cdot n) /$$

$$(k\lambda_1 \cdot \eta F\lambda_1 \cdot n + k\lambda_2 \cdot \eta F\lambda_2 \cdot N)$$

By this division operation, the non-uniformity I$\lambda_{ex}$ of the irradiance of the excitation light, depending upon sites, is canceled. Therefore, in this structure wherein the long wavelength component (for example, the red wavelength component R) among the intrinsic fluorescence is divided by the fluorescence sum component (for example, G+R), which is the sum of the short wavelength component (for example, the green wavelength component G) and the long wavelength component (i.e., in cases where the fluorescence sum component If$\lambda_+$ is used as the denominator in the division), the value of the denominator can be kept large. Therefore, the occurrence of an operation error due to division by the value of zero can be restrained. Accordingly, for example, if an image sensor is employed as each of the fluorescence detecting means 3 and the fluorescence detecting means 4, a fluorescence image, in which the intensity of fluorescence has been corrected, can be displayed as a visible image on the display means 6.

The fluorescence detecting apparatus in accordance with the present invention is also applicable when a fluorescence difference component is divided by the fluorescence sum component.

A structure of the apparatus described below is designed for the cases where the fluorescence with the administration of the drug is detected. Also, in this structure, the fluorescence difference component (In−Ex), which is the difference between the intrinsic fluorescence In and the extrinsic fluorescence component Ex, is divided by the fluorescence sum component (In+Ex), which is the sum of the intrinsic fluorescence component In and the extrinsic fluorescence component Ex. The structure will hereinbelow be described in detail.

In this structure, as in the aforesaid cases where the fluorescence with the administration of the drug is detected, the fluorescence L3 produced from the region of interest 10 in the living body is received by the fluorescence receiving optical system 2. The fluorescence L3 is separated with respect to wavelength ranges by a dichroic mirror, an optical filter, or the like. The fluorescence difference component, which is the difference between the intrinsic fluorescence and the extrinsic fluorescence component having been produced from the region of interest 10 in the living body, and the fluorescence sum component, which is the sum of the intrinsic fluorescence component and the extrinsic fluorescence component, are thereby separated from each other. The fluorescence detecting means 3 detects the fluorescence difference component, and the fluorescence detecting means 4 detects the fluorescence sum component. The other features are the same as those in the aforesaid cases where the fluorescence with the administration of the drug is detected. The wavelength range of the intrinsic fluorescence component, which is used in the detection of the fluorescence difference component, and the wavelength range of the intrinsic fluorescence component, which is contained in the fluorescence sum component, need not necessarily be identical with each other. Also, the wavelength range of the extrinsic fluorescence component, which is used in the detection of the fluorescence difference component, and the wavelength range of the extrinsic fluorescence component, which is contained in the fluorescence sum component, need not necessarily be identical with each other. Further, as in the aforesaid cases, the means for detecting the fluorescence difference component and the means for detecting the fluorescence sum component are not limited to those employed in this structure. As an alternative, fluorescence components each covering wavelengths falling within a predetermined wavelength range may be separated from each other and detected, and a fluorescence component covering wavelengths falling within a wavelength range to be used ultimately maybe calculated by carrying out an operation, such as addition or subtraction, on the results of the detection. How the fluorescence detecting apparatus having the structure described above operates will be described hereinbelow.

The wavelength components detected by the fluorescence detecting means 3 and the fluorescence detecting means 4 may be represented as described below. As is clear from the foregoing, the fluorescence sum component If$\lambda_+$ may be represented by the formula shown below.

$$\text{If } \lambda_+ = \text{If } \lambda_2 + \text{If } \lambda_1$$
$$= (k\lambda_2 \cdot I\lambda_{ex} \cdot \eta F\lambda_2 \cdot n \cdot \eta D) + (k\lambda_1 \cdot I\lambda_{ex} \cdot \eta F\lambda_1 \cdot N \cdot \eta D)$$

The fluorescence difference component If$\lambda_-$ may be represented by the formula shown below.

$$\text{If } \lambda_- = \text{If } \lambda_2 - \text{If } \lambda_1$$
$$= (k\lambda_2 \cdot I\lambda_{ex} \cdot \eta F\lambda_2 \cdot n \cdot \eta D) - (k\lambda_1 \cdot I\lambda_{ex} \cdot \eta F\lambda_1 \cdot N \cdot \eta D)$$

Thereafter, the division means 5 carries out the division operation of the fluorescence difference component If $\lambda_-$ by the fluorescence sum component If$\lambda_+$. The division operation may be represented by the formula shown below.

$$\text{If } \lambda_- / \text{If } \lambda_+ = (k\lambda_2 \cdot I\lambda_{ex} \cdot \eta F\lambda_2 \cdot n \cdot \eta D) -$$
$$(k\lambda_1 \cdot I\lambda_{ex} \cdot \eta F\lambda_1 \cdot N \cdot \eta D) / (k\lambda_2 \cdot I\lambda_{ex} \cdot \eta F\lambda_2 \cdot n \cdot \eta D) +$$
$$(k\lambda_1 \cdot I\lambda_{ex} \cdot \eta F\lambda_1 \cdot N \cdot \eta D)$$
$$= (k\lambda_2 \cdot \eta F\lambda_2 \cdot n - k\lambda_1 \cdot \eta F\lambda_1 \cdot N) /$$
$$(k\lambda_2 \cdot \eta F\lambda_2 \cdot n + k\lambda_1 \cdot \eta F\lambda_1 \cdot N)$$

If $(k\lambda_1 \cdot \eta F\lambda_1)/(k\lambda_2 \cdot \eta F\lambda_2) = C$ and $N/n = X$, the formula shown below will be obtained.

$$\text{If}\lambda_- / \text{If}\lambda_+ = (1 - C \cdot X)/(1 + C \cdot X)$$

Specifically, in this structure, the non-uniformity I$\lambda_{ex}$ Of the irradiance of the excitation light, depending upon sites, is canceled. The value of X represents the concentration of the extrinsic fluorescent molecules having been normalized with the concentration of the intrinsic fluorescent molecules. A large value of If$\lambda_-$/If$\lambda_+$ indicates that the extrinsic fluorescence is weak and that the region of interest is located at the normal part. Conversely, a small value of If$\lambda_-$/If$\lambda_+$ indicates that the extrinsic fluorescence is strong and that the region of interest is located at the diseased part. In this manner, the diseased part can be detected specifically by carrying out the division operation of the fluorescence difference component If$\lambda_-$ by the fluorescence sum component If$\lambda_+$. In cases where the fluorescence sum component If$\lambda_+$ is used as the denominator in the division, the value of the denominator can be kept large, and therefore the occurrence of an operation error due to division by the value of zero can be restrained.

The structure described above is designed for the cases where the fluorescence with the administration of the drug is detected. The same idea as that of the structure described above is also applicable to the cases where the autofluorescence without the administration of the drug is detected. In this structure, the fluorescence difference component in the fundamental structure maybe replaced by a fluorescence difference component (for example, G−R), which is the difference between the short wavelength component (for example, the green wavelength component G) and the long wavelength component (for example, the red wavelength component R). Also, the fluorescence sum component in the fundamental structure may be replaced by the fluorescence sum component (for example, G+R), which is the sum of the short wavelength component (for example, the green wavelength component G) and the long wavelength component (for example, the red wavelength component R). In the structures described above, the fluorescence sum component is employed in the division. The fluorescence detecting apparatus in accordance with the present invention is also applicable when a fluorescence component covering wavelengths falling within approximately the entire wavelength range of the fluorescence (i.e., an entire fluorescence component), the fluorescence being produced from the region of interest 10 in the living body when the region of interest 10 is exposed to the excitation light, is employed in the division. Structures for such cases will hereinbelow be described in detail.

A structure described below is designed for the cases where the autofluorescence without the administration of the drug is detected. In this structure, the fluorescence difference component (for example, G–R), which is the difference between the short wavelength component (for example, the green wavelength component G) and the long wavelength component (for example, the red wavelength component R), is divided by an entire fluorescence component.

As in the structures described above, wherein the fluorescence sum component is employed in the division operation, the intrinsic fluorescence L3 produced from the region of interest in the living body is received by the fluorescence receiving optical system 2. The intrinsic fluorescence L3 is separated with respect to wavelength ranges by a dichroic mirror, an optical filter, or the like. A fluorescence difference component If $\lambda_-$, which is the difference between the short wavelength component If$\lambda_2$ and the long wavelength component If$\lambda_1$, and an entire fluorescence component If$\lambda_{12}$, which contains the short wavelength component If$\lambda_2$ and the long wavelength component If$\lambda_1$, are thereby separated from each other. The fluorescence detecting means 3 detects the fluorescence difference component If$\lambda_-$, and the fluorescence detecting means 4 detects the entire fluorescence component If$\lambda_{12}$. The other features are the same as those in the aforesaid structures. As in the aforesaid structures, the means for detecting the fluorescence difference component and the means for detecting the entire fluorescence component are not limited to those employed in this structure. In particular, the means for detecting the entire fluorescence component may be constituted in the manner described below. That is, the characteristics of wavelength separation between the short wavelength component and the long wavelength component may be devised specifically (such that, for example, the cut-off characteristics on the long-wavelength side of the short wavelength component and the cut-off characteristics on the short-wavelength side of the long wavelength component may be identical with each other), so that the short wavelength component and the long wavelength component may thereby be separated from each other and detected. The results of the detection may then be added to each other, and a fluorescence sum component may thereby be obtained. The thus obtained fluorescence sum component may be employed as the entire fluorescence component. In such cases, the process for carrying out the division operation using the fluorescence sum component described above can directly function as the process for carrying out the division operation using the entire fluorescence component. Such a process of detecting the entire fluorescence component may also be employed in the structures described later.

How the fluorescence detecting apparatus having the fundamental structure 5 described above operates will be described hereinbelow. The wavelength components detected by the fluorescence detecting means 3 and the fluorescence detecting means 4 may be represented as described below. As is clear from the foregoing, the fluorescence difference component If$\lambda_-$ may be represented by the formula shown below.

$$\text{If } \lambda_- = \text{If } \lambda_2 - \text{If } \lambda_1$$
$$= (k\lambda_2 \cdot I\lambda_{ex} \cdot \eta F\lambda_2 \cdot N \cdot \eta D) - (k\lambda_1 \cdot I\lambda_{ex} \cdot \eta F\lambda_1 \cdot n \cdot \eta D)$$

The entire fluorescence component If$\lambda_{12}$ covering wavelengths falling within the wavelength range, which contains both the short wavelength range and the long wavelength range, may be represented by the formula shown below.

$$\text{If}\lambda_{12} = k\lambda_{12} \cdot I\lambda_{ex} \cdot \eta F\lambda_{12} \cdot M \cdot \eta D$$

Thereafter, the division means 5 carries out the division operation of the fluorescence difference component If $\lambda_-$ by the entire fluorescence component If$\lambda_{12}$. The division operation may be represented by the formula shown below.

$$\text{If } \lambda_- / \text{If } \lambda_{12} = (k\lambda_2 \cdot I\lambda_{ex} \cdot \eta F\lambda_2 \cdot N \cdot \eta D) - (k\lambda_1 \cdot I\lambda_{ex} \cdot \eta F\lambda_1 \cdot n \cdot \eta D) /$$
$$(k\lambda_{12} \cdot I\lambda_{ex} \cdot \eta F\lambda_{12} \cdot M \cdot \eta D)$$
$$= k\lambda_2 \cdot \eta F\lambda_2 \cdot N / k\lambda_{12} \cdot \eta F\lambda_{12} \cdot M -$$
$$k\lambda_1 \cdot \eta F\lambda_1 \cdot n / k\lambda_{12} \cdot \eta F\lambda_{12} \cdot M$$
$$= (C_1 / M) \cdot (N - C_2 \cdot M)$$

where each of $C_1$ and $C_2$ is a constant.

Specifically, in this structure, the non-uniformity $I\lambda_{ex}$ of the irradiance of the excitation light, depending upon sites, is canceled. A large value of If$\lambda_-$/If$\lambda_{12}$ indicates that the fluorescence covering wavelengths falling within the short wavelength range is strong and that the region of interest is located at the normal part. Conversely, a small value of If $\lambda_-$/If$\lambda_{12}$ indicates that the fluorescence covering wavelengths falling within the short wavelength range is weak and that the region of interest is located at the diseased part. In this manner, the diseased part can be detected specifically by carrying out the division operation of the fluorescence difference component If$\lambda_-$ by the entire fluorescence component If$\lambda_{12}$. In cases where the entire fluorescence component If$\lambda_{12}$ is used as the denominator in the division operation, the value of the denominator can be kept large, and therefore the occurrence of an operation error due to division by the value of zero can be restrained.

The structure described above is designed for the cases where the autofluorescence without the administration of the drug is detected, and the fluorescence difference component (for example, G–R), which is the difference between the short wavelength component (for example, the green wavelength component G) and the long wavelength component (for example, the red wavelength component R), is divided by the entire fluorescence component. The same idea as that in the structure described above is also applicable when the long wavelength component (for example, the red wavelength component R) is divided by the entire fluorescence component, or when the short wavelength component (for example, the blue wavelength component B) is divided by the entire fluorescence component. In such cases, the fluorescence difference component in the structure described above may be replaced by either of the long wavelength component or the short wavelength component.

The two last-described structures are designed for the cases where the autofluorescence without the administration of the drug is detected. The same ideas as those in the two last-described structures are also applicable to the cases where the fluorescence with the administration of the drug is detected.

In such cases, the division operation of the fluorescence difference component by the entire fluorescence component may be replaced by the division operation of the fluorescence difference component (In−Ex), which is the difference between the intrinsic fluorescence component In and the extrinsic fluorescence component Ex, by the entire fluorescence component. Also, the division operation of the long wavelength component by the entire fluorescence component in the structure described above may be replaced by the division operation of the extrinsic fluorescence component Ex by the entire fluorescence component.

A first embodiment of the fluorescence detecting apparatus in accordance with the present invention will be described hereinbelow.

Figure 6:
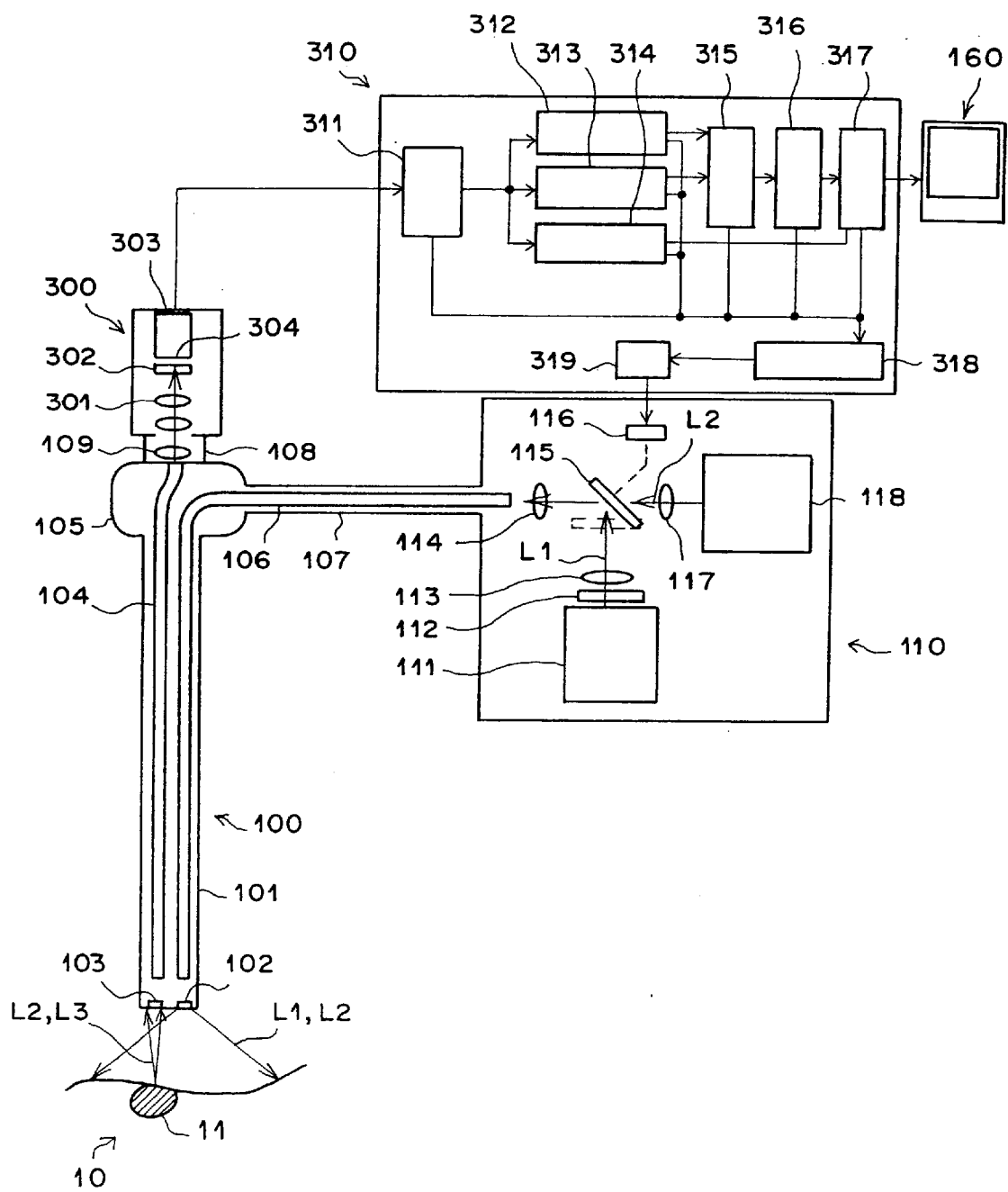
FIG. 6 is a schematic view showing an endoscope system, in which a fluorescence detecting apparatus according to a first embodiment of the present invention is employed.

FIG. 6 is a schematic view showing an endoscope system, in which a first embodiment of the fluorescence detecting apparatus in accordance with the present invention is employed. In this endoscope system, excitation light is irradiated to a region of interest in a living body, to which a fluorescent diagnosis drug has been administered, so that the fluorescence, which is produced from the region of interest in the living body when the region of interest is exposed to the excitation light, is detected. Also, a red fluorescence component is divided by a fluorescence sum component, which is the sum of a blue fluorescence component, a green fluorescence component, and the red fluorescence component.

The endoscope system, in which the first embodiment of the fluorescence detecting apparatus in accordance with the present invention is employed, comprises: the endoscope 100 to be inserted into a region of a patient, the region being considered as being a diseased part; and the illuminating device 110 provided with the light sources for producing white light, which is used when an ordinary image is to be obtained, and the excitation light, which is used when a fluorescence image is to be obtained. The endoscope system also comprises a high-sensitivity camera unit 300 for detecting the white light, which is reflected from the region of interest 10 in the living body when the ordinary image is to be obtained, and for detecting the fluorescence, which is produced from the region of interest 10 in the living body when the fluorescence image is to be obtained. The endoscope system further comprises: an image processing unit 310 for carrying out image processing on an image signal, which represents the reflected light image or the fluorescence image having been detected; and the display device 160 for reproducing a visible image from the image signal, which has been obtained from the image processing carried out by the image processing unit 310, and for displaying the reproduced visible image.

The endoscope 100 is provided with an endoscope tube 101, which is to be inserted into the living body. A light guide 106 and image fibers 104 extend in the endoscope tube 101 up to a leading end of the endoscope tube 101. An illuminating lens 102 is located at a leading end of the light guide 106, i.e. at the leading end of the endoscope tube 101. An objective lens 103 is located at a leading end of the image fibers 104, i.e. at the leading end of the endoscope tube 101. A tail end portion of the light guide 106 passes through a connecting section 107 for connecting the illuminating device 110 and a manipulating section 105 and extends into the illuminating device 110. A tail end portion of the image fibers 104 extends into the manipulating section 105, and its tail end is in contact with an eyepiece section 108, which is provided with an eyepiece 109.

The illuminating device 110 comprises a xenon lamp 118 for producing the white light L2 for obtaining the ordinary image, and a mercury vapor lamp 111 for producing the excitation light L1 for obtaining the fluorescence image. The illuminating device 110 also comprises an optical filter 112 for specifying the transmission wavelength of the excitation light L1 having been produced by the mercury vapor lamp 111, and a switching mirror 115, which is operated by a driver 116 and switches between the white light L2 for obtaining the ordinary image and the excitation light L1 for obtaining the fluorescence image.

The high-sensitivity camera unit 300 comprises an excitation light sharp cut filter 302, which transmits the reflected white light when the ordinary image is to be obtained, and which filters out the excitation light component of the fluorescence L3 when the fluorescence image is to be obtained. The high-sensitivity camera unit 300 also comprises a cold CCD camera 303 as the detecting means, on which the image of the reflected white light having passed through the filter 302 or the image of the fluorescence L3 having passed through the filter 302 is formed. Fixed on the detection surface of the cold CCD camera 303 is a color mosaic filter 304 including filter elements of primary colors (i.e., red (R), green (G) and blue(B) filter elements) schematically illustrated in FIG. 7. The fluorescence is separated into three wavelength components (i.e., the components corresponding to red, green and blue wavelength ranges) through the R, G and B filter elements of the color mosaic filter 304. FIG. 8 shows optical transmission characteristics of the R, G and B filter elements.

The image processing unit 310 comprises an analog-to-digital conversion circuit 311 for digitizing the image signals having been obtained from the cold CCD camera 303. The image processing unit 310 also comprises an R image memory 314 for storing a digitized R image signal, a G image memory 313 for storing a digitized G image signal, and a B image memory 312 for storing a digitized B image signal. The image processing unit 310 further comprises: an addition memory 315 for storing an addition signal, which represents the fluorescence sum component obtained by adding the outputs from the image memories to one another; and a division memory 316 for carrying out a division operation of the output from the R image memory 314 by the output from the addition memory 315 and for storing the information representing the results of the division. The image processing unit 310 still further comprises a video signal forming circuit 317 for carrying out image processing on the ordinary image signals, which are received from the image memories 312, 313, and 314, or on the division image signal, which is received from the division memory 316, to thereby obtain a video signal to be used for reproducing the visible image on the display device 160. The image processing unit 310 also comprises: a timing controller 319 for feeding a signal into the driver 116, which drives the switching mirror 115 of the illuminating device 110; and a video processor 318 for controlling the timing controller 319.

How the endoscope system, in which the first embodiment of the fluorescence detecting apparatus in accordance with the present invention is employed, operates will be described hereinbelow. Firstly, how the endoscope system operates when the ordinary image is to be obtained will be described hereinbelow.

When the ordinary image is to be obtained, the switching mirror 115 of the illuminating device 110 is driven by the driver 116 in accordance with the signal fed from the timing controller 158 and is moved to the position indicated by the broken line in FIG. 6, such that the switching mirror 115 may not obstruct the travelling path of the white light L2.

The white light L2 having been produced by the xenon lamp 118 passes through a lens 117 and travels to the switching mirror 115. The white light L2 is caused by a lens 114 to enter the light guide 106, guided through the light guide 106 to the leading end of the endoscope 100, and then irradiated through the illuminating lens 102 to the region of interest 10 in the living body containing the diseased part 11.

The white light L2, which has been reflected from the region of interest 10 in the living body, is collected by the objective lens 103 and passes through the image fibers 104 and the eyepiece 109, which is located in the eyepiece section 108. The reflected white light L2 then travels to the high-sensitivity camera unit 300. The reflected white light L2, which has passed through the eyepiece 109, passes through a lens 301 and the excitation light sharp cut filter 302, and the image of the reflected white light L2 is formed on the cold CCD camera 303. As the color mosaic filter 304 is fixed on the detection surface of the cold CCD camera 303, the light is separated into red (R), green (G) and blue(B) wavelength components. The image signal obtained from the cold CCD camera 303 is fed into the analog-to-digital conversion circuit 311. The analog-to-digital conversion circuit 311 digitizes each of R, G, and B image signals, and the thus obtained digital R, G, and B image signals are stored respectively in the R image memory 314, the G image memory 313, and the B image memory 312. The ordinary image signals, which have thus been stored in the R image memory 314, the G image memory 313, and the B image memory 312, are then fed into the video signal forming circuit 317. In the video signal forming circuit 317, the ordinary image signals are subjected to digital-to-analog conversion, color matrix processing, and encoding. The ordinary image signals having been obtained from the processing are then fed as NTSC signals into the display device 160. The display device 160 reproduces the visible image from the signals and displays it.

How the endoscope system, in which the first embodiment of the fluorescence detecting apparatus in accordance with the present invention is employed, operates when the fluorescence image is to be obtained will be described hereinbelow. In this embodiment, 5-ALA capable of producing the fluorescence having a wavelength of approximately $\lambda_{em}$=635 nm is employed as the fluorescent diagnosis drug. The fluorescent diagnosis drug 5-ALA has been administered to the region of interest 10 in the living body.

The switching mirror 115 of the illuminating device 110 is driven by the driver 116 in accordance with the signal fed from the timing controller 158 and is moved to the position indicated by the solid line in FIG. 6, such that the switching mirror 115 may block the travelling path of the white light L2 and may reflect the excitation light L1. The excitation light L1 having been produced by the mercury vapor lamp 11 passes through the optical filter 112 and a lens 113 and travels to the switching mirror 115. The excitation light L1 is then reflected by the switching mirror 115 and caused by the lens 114 to enter the light guide 106. The excitation light L1 is guided through the light guide 106 to the leading end of the endoscope 100, and then irradiated through the illuminating lens 102 to the region of interest 10 in the living body containing the diseased part 11. The optical filter 112 has the transmission characteristics as illustrated in FIG. 9, and the excitation light L1, which has been produced by the mercury vapor lamp 111 and has passed through the optical filter 112, has the line spectrum of the wavelength of 405 nm.

The fluorescence L3, which is produced from the region of interest 10 in the living body when the region of interest is exposed to the excitation light L1, is collected by the objective lens 103 and passes through the image fibers 104 and the eyepiece 109. The fluorescence L3 then passes through the excitation light sharp cut filter 302, which filters out the excitation light component. After the fluorescence L3 is separated into the R, G and B wavelength components through the color mosaic filter 304 fixed on the detection surface of the cold CCD camera, the red, green and blue images of the fluorescence L3 are formed on the cold CCD camera 303. The intensity of the fluorescence L3 is lower than the intensity of the reflected white light L2. Therefore, when the fluorescence image is to be obtained, the imaging rate of the cold CCD camera 303 is set to be sufficiently lower than the imaging rate for obtaining the ordinary image. The fluorescence image signal obtained from the cold CCD camera 303 is fed into the analog-to-digital conversion circuit 311. The analog-to-digital conversion circuit 311 digitizes each of R, G, and B image signals, and the thus obtained digital R, G, and B image signals are stored respectively in the R image memory 314, the G image memory 313, and the B image memory 312. After the image signals representing the R, G, and B fluorescence images have thus been obtained, the addition memory 315 carries out the addition operation of the outputs, which are obtained from the R image memory 314, the G image memory 313, and the B image memory 312. The result of the addition operation is stored as the addition signal, which represents the fluorescence sum component, in the addition memory 315. In the fluorescence produced from the living body, the R image signal mainly represents the extrinsic fluorescence, and the B and G image signals mainly represent the intrinsic fluorescence. Therefore, the results of the addition operation represent the sum of the extrinsic fluorescence and the intrinsic fluorescence.

Thereafter, the division memory 316 carries out the division operation of the output fed from the R image memory 212 by the output fed from the addition memory 315. The result of the division operation (i.e., a division image signal) is stored in the division memory 316. The division image signal is then fed into the video signal forming circuit 317. In the video signal forming circuit 317, the division image signal is subjected to digital-to-analog conversion and encoding. The division image signal having been obtained from the processing is then fed into the display device 160. The display device 160 reproduces a visible image (a division image) from the division image signal and displays it. When necessary, a memory for storing the ordinary image signal maybe employed besides the R, G and B image memories, and the visible ordinary image and the visible division image may be overlaid one upon the other on the display device 160.

Figure 10:
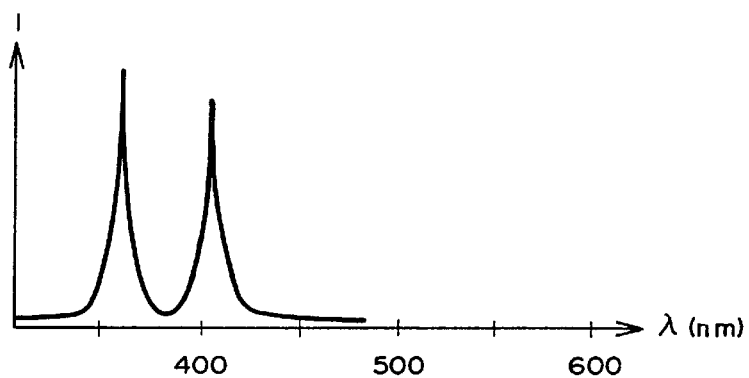
FIG. 10 is a graph showing another example of an excitation light spectrum of the excitation light emitted by the excitation light source in the first embodiment.

The optical filter 112 located on the mercury vapor lamp 111 may be replaced by an optical filter having different transmission characteristics. For example, as illustrated in FIG. 10, an optical filter capable of selectively transmitting light having a line spectrum of 405 nm and light having a line spectrum of 365 nm may be employed as the optical filter 112. The wavelength of 405 nm is a wavelength $\lambda_{ex1}$ capable of exciting the fluorescent diagnosis drug with a high efficiency, and the wavelength of 365 nm is a wavelength $\lambda_{ex2}$ capable of exciting an intrinsic fluorescence molecules with a high efficiency. Therefore, the combined use of the two kinds of light is desirable for enhancing the signal-to-noise ratio. This also applies to the below-described cases where the fluorescence with the administration of the drug is detected.

In this embodiment, since the intrinsic fluorescence has a high intensity in the G wavelength range, the addition operation for obtaining the sum of the intrinsic fluorescence component and the extrinsic fluorescence component may be replaced by the addition operation of the output from the G image memory 313 and the output from the R image memory 314.

In this embodiment, the color mosaic filter has the wavelength separation characteristics illustrated in FIG. 8.

Therefore, it may be considered that the detection of the fluorescence sum component is substantially equivalent to the detection of the entire fluorescence component. In such cases, the wavelength separation characteristics of the color mosaic filter 304 may be altered (such that, for example, the cut-off characteristics for the respective colors may not overlap one upon another). In this manner, the fluorescence sum component, which is not equivalent to the entire fluorescence component, may be obtained in the addition memory 315, and the division operation of the R fluorescence component by the thus obtained fluorescence sum component may be carried out in the division memory 316.

After the fluorescence is separated into the R, G and B wavelength components through the color mosaic filter 304 fixed on the detection surface of the high-sensitivity camera unit 300, it is now possible to detect a plurality of desired wavelength components of the fluorescence using a single cold CCD camera 303. Thus, it becomes possible to provide a fluorescence detecting apparatus with a compact configuration requiring a relatively low operation cost.

With such a compact configuration realized by use of the color mosaic filter 304, a CCD camera equipped with the color mosaic filter 304 fixed thereon can be easily attached to the tip of the endoscope. That is to say, an electronic endoscope equipped with an image sensor attached thereon can be provided according to the present embodiment. As the color mosaic filter 304 in the present embodiment includes the filter elements of primary colors, each fluorescence component can be extracted and detected requiring only simple signal processing. The sharp cut filter used in the present embodiment may be modified in accordance with the wavelength range of the excitation light.

In the present embodiment, the fluorescence with the administration of the drug is detected. However, the present embodiment is also applicable to autofluorescence diagnosing systems, in which the autofluorescence without the administration of the drug is detected. In such cases, each of the structures of the present embodiment may be applied almost directly. In such cases, light covering wavelengths, which fall within a wavelength range in the vicinity of the excitation peak wavelength for the intrinsic dye in the living body, may be employed as the excitation light.

In the present embodiment, the division operation of the extrinsic fluorescence component or the long wavelength component (for example, the red fluorescence component R) is carried out. However, the fluorescence detecting apparatus in accordance with the present invention is also applicable when the division operation of the short wavelength component (for example, the blue fluorescence component B) is carried out. The fluorescence detecting apparatus in accordance with the present invention is also applicable when the division of a fluorescence difference component, (In−Ex) or (G−R), is carried out.

Figure 12:
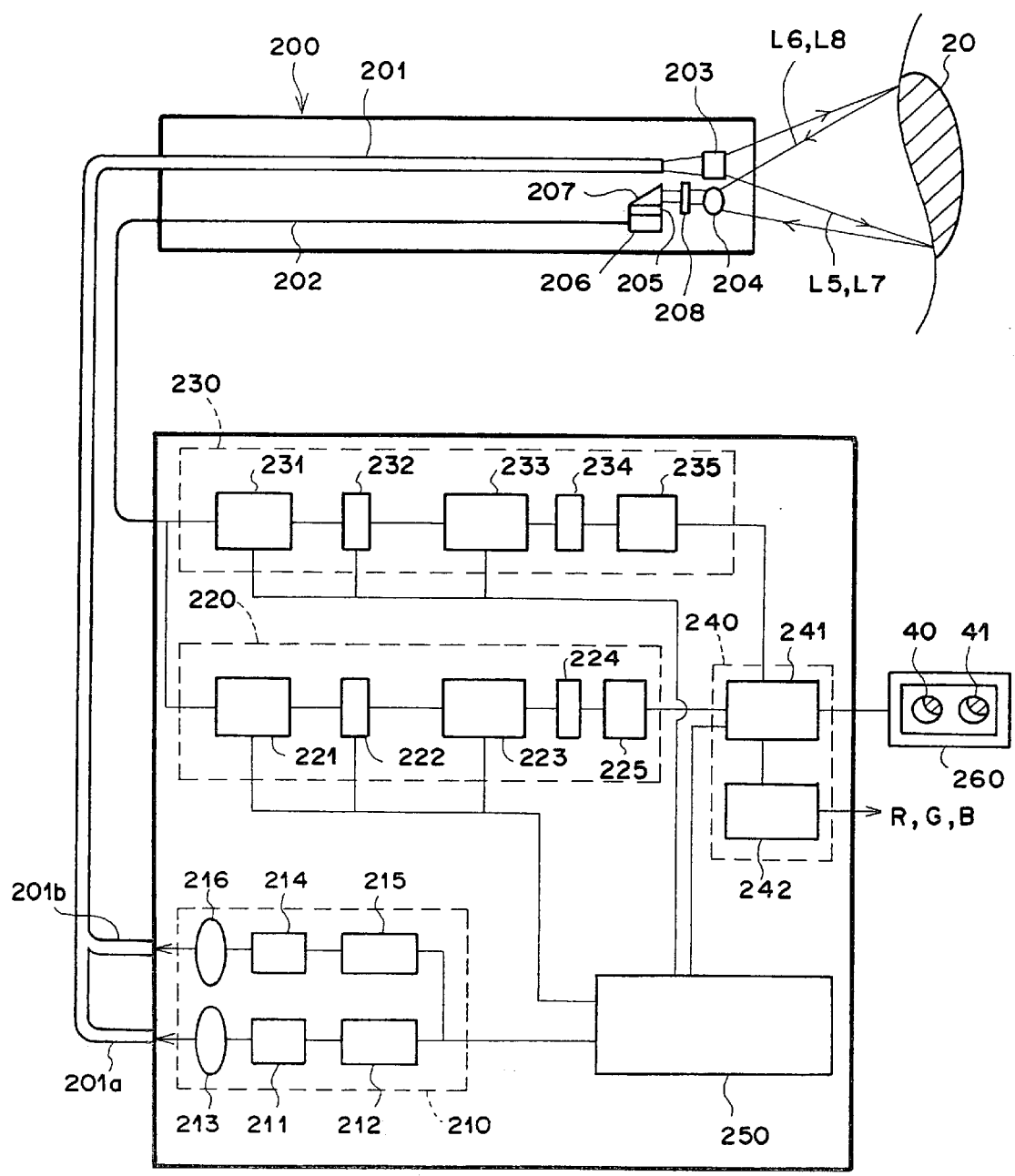
FIG. 12 is a schematic view showing an endoscope system, in which a fluorescence detecting apparatus according to a second embodiment of the present invention is employed.

Now, another endoscope system according to a second embodiment of the present invention will be described referring to FIGS. 12 and 13. FIG. 12 is a schematic view showing the endoscope system, in which a fluorescence detecting apparatus according to the second embodiment of the present invention is employed. In this endoscope system, the excitation light is irradiated to a region of interest 20 in a living body causing the region of interest 20 to produce fluorescence. The produced florescence is detected by a CCD image sensor fixed to the tip of the endoscope so that a fluorescence image is displayed. The CCD image sensor is also used for obtaining an ordinary image.

The endoscope system, in which the fluorescence detecting apparatus according to the second embodiment of the present invention is employed, comprises: an endoscope 200 to be inserted into a region of a patient considered to be a diseased part; and an illuminating unit 210 provided with light sources for producing white light L5, which is used when an ordinary image is to be detected, and the excitation light L7, which is used when a fluorescence image is to be detected. The endoscope system also comprises: a fluorescence image processing unit 220 for performing image processing for displaying the fluorescence image as a pseudo color image; and an ordinary image processing unit 230 for performing image processing for displaying an ordinary image as a color image. The endoscope system further comprises a display image processing unit 240 for superimposing the color image of the ordinary image and the pseudo color image of the fluorescence image one upon the other. The endoscope system also comprises a controller 250, which is connected to the respective units for controlling operation timings. The endoscope system still further comprises a monitor 260 for displaying the ordinary image (specifically, the color image of the ordinary image) and the fluorescence image (specifically, the pseudo color image of the fluorescence image), which have been superimposed one upon the other by the display image processing unit 240.

A light guide 201 and a CCD cable 202 extend in the endoscope 200 up to a leading end of the endoscope 200. An illuminating lens 203 is located at a leading end of the light guide 201, i.e. at the leading end of the endoscope 200. An objective lens 204 is located at a leading end of the CCD cable 202, i.e. at the leading end of the endoscope 200. A CCD image sensor 206 including a cold CCD cameara of a back-exposure type is fixed to the leading end of the CCD cable 202. A color mosaic filter 205, which comprises a plurality of fine band-pass filter elements arrayed in a mosaic-like form, is fixed on the cold CCD camera. Also, a prism 207 is mounted on the CCD image sensor 206. An excitation light cut filter 208 is provided at a position between the objective lens 204 and the prism 207 to thereby cut the light having a wavelength of 430 nm or less, i.e., the light having the wavelength close to that of the excitation light.

The color mosaic filter 205 is a complementary color type of filter including filter elements of complementary colors. That is, as shown in FIG. 13, the colormosaic filter 205 includes: yellow filter elements 205a for transmitting a light component having a wavelength of 510 nm or more; cyan filter elements 205b for transmitting a light component having a wavelength of 600 nm or less; and magenta filter elements for transmitting a light component having a wavelength of 510 nm or less or a wavelength of 600 nm or more.

The light guide 201 comprises a white light guide 201a, which is constituted of a compound glass fiber, and an excitation light guide 201b, which is constituted of a quartz glass fiber. The white light guide 201a and the excitation light guide 201b are bundled together in a cable-like form to constitute the light guide 201. The white light guide 201a and the excitation light guide 201b are connected to the illuminating unit 210. A tail end of the CCD cable 202 is connected to the fluorescence image processing unit 220 and the ordinary image processing unit 230.

The illuminating unit 210 comprises a white light source 211 for producing white light L1, which is used when an ordinary image is to be detected, and an electric power source 212, which is electrically connected to the white light source 211. The illuminating unit 210 also comprises a GaN type of semiconductor laser 214 for producing excitation light L3, which is used when a fluorescence image is to be detected, and an electric power source 215, which is electrically connected to the GaN type of semiconductor laser 214.

The fluorescence image processing unit 220 comprises a signal processing circuit 221 for forming pseudo color image signals from the fluorescence image, which has been detected by the CCD image sensor 206. The fluorescence image processing unit 220 also comprises an analog-to-digital converting circuit 222 for digitizing the pseudo color image signals, which have been obtained from the signal processing circuit 221. The fluorescence image processing unit 220 further comprises a fluorescence image memory 223 for storing the digital pseudo color image signals, which have been obtained from the analog-to-digital converting circuit 222. The fluorescence image processing unit 220 still further comprises a digital-to-analog converting circuit 224 for performing digital-to-analog conversion on the pseudo color image signals, which have been received from the fluorescence image memory 223. The fluorescence image processing unit 220 also comprises a fluorescence image encoder 225 for transforming the pseudo color image signals, which have been received from the digital-to-analog converting circuit 224, into video signals.

The signal processing circuit 221 first processes the signals obtained from the CCD image sensor 206 in a predetermined manner. Then, the signal processing circuit 221 calculates the signal intensity corresponding to the blue wavelength range and the total signal intensity corresponding to the entire wavelength range. The calculation is based on the signal intensities of the fluorescence components each transmitted by the yellow filter elements 205a, cyan filter elements 205b or magenta filter elements 205c, respectively. Thereafter, the signal processing circuit 221 forms the pseudo color image signals based on the signal intensity corresponding to the blue wavelength range and the total signal intensity corresponding to the entire wavelength range.

The ordinary image processing unit 230 comprises a signal processing circuit 231 for forming color image signals from the ordinary image, which has been detected by the CCD image sensor 206. The ordinary image processing unit 230 also comprises an analog-to-digital converting circuit 232 for digitizing the color image signals, which have been obtained from the signal processing circuit 231. The ordinary image processing unit 230 further comprises an ordinary image memory 233 for storing the digital color image signals, which have been obtained from the analog-to-digital converting circuit 232. The ordinary image processing unit 230 still further comprises a digital-to-analog converting circuit 234 for performing digital-to-analog conversion on the color image signals, which have been received from the ordinary image memory 233. The ordinary image processing unit 230 also comprises an ordinary image encoder 235 for transforming the color image signals, which have been received from the digital-to-analog converting circuit 234, into video signals.

The display image processing unit 240 comprises a superimposer 241 for superimposing the pseudo color image signals, which have been received from the fluorescence image encoder 225, onto the color image signals, which have been received from the ordinary image encoder 235, and for outputting the thus obtained image signals as the display signals. The display image processing unit 240 also comprises an RGB decoder 242 for transforming the display signals, which are the video signals, into R, G and B color signals. That is to say, the RGB decoder 242 calculates the superimposed pseudo color image signals and the color image signals backward into the R, G and B color signals, so that the R, G and B color signals are outputted to a printer, an image processing apparatus, etc., capable of directly receiving the color signals as inputs.

How the endoscope system, in which the fluorescence detecting apparatus according to the present embodiment, operates will be described hereinbelow. Firstly, how the endoscope system operates when an ordinary image is to be displayed will be described hereinbelow.

When an ordinary image is to be displayed, the electric power source 212 for the white light source 211 is driven in accordance with a control signal fed from the controller 250, and the white light L5 is produced by the white light source 211. The white light L5 passes through a lens 213 and impinges upon the white light guide 201a. The white light L5 is guided through the white light guide 201a to the leading end of the endoscope 200, passes through the illuminating lens 203, and is irradiated to a region of interest 20. The white light L5 is reflected as reflected light L6 from the region of interest 20. The reflected light L6 is converged by the objective lens 204 and reflected by the prism 207. The reflected light L2 then passes through the color mosaic filter 205, and is received by the CCD image sensor 206.

In the signal processing circuit 231, the processing, such as correlative double sampling, clamping, blanking, and amplification, are performed on the signals having been obtained from the CCD image sensor 206. Thereafter, complementary-color/primary-color transform is performed in a pixel-by-pixel manner to calculate signal intensities of primary color components (i.e., the signal intensity B2 corresponding to the blue wavelength range, the signal intensity G2 corresponding to the green wavelength range and the signal intensity R2 corresponding to the red wavelength range) from the signal intensities of the complementary color components (i.e., the signal intensity Ye2 of the yellow (or green+red) wavelength range transmitted by the yellow filter components 205a, the signal intensity Cy2 of the cyan (or blue+green) wavelength range transmitted by the cyan filter components 205b, and the signal intensity Mg2 of the magenta (or blue+red) wavelength range transmitted by the magenta filter components 205c). Calculation for any pixel requires use of adjacent pixel values thereof. Specifically, the calculation is carried out using the following equations.

$$W2(Ye2+Cy2+Mg2)/2$$

$$R2=W2-Cy2$$

$$G2=W2+Mg2$$

$$B2=W2-Ye2$$

Further, the color image signals are calculated from the above signal intensities of primary color components (i.e., the signal intensity B2 corresponding to the blue wavelength range, the signal intensity G2 corresponding to the green wavelength range and the signal intensity R2 corresponding to the red wavelength range).

The color image signals for individual pixels calculated by the signal processing circuit 231 are digitized by the analog-to-digital converting circuit 232. The thus digitized color image signals are stored in the ordinary image memory 233. In accordance with a display timing, the color image signals having been stored in the ordinary image memory 233 are subjected to the digital-to-analog conversion in the digital-to-analog converting circuit 234 and transformed by the ordinary image encoder 235 into predetermined video signals. The thus obtained video signals are fed into the superimposer 241 and superimposed upon the pseudo color image signals, which are obtained in the manner described later. The superimposed video signals are fed into the monitor 260.

Now, how the above endoscope system operates when a fluorescence image is to be displayed will be described hereinbelow.

When a fluorescence image is to be displayed, the electric power source 215 for the GaN type of semiconductor laser 214 is driven in accordance with a control signal fed from the controller 250, and the excitation light L7 having a wavelength of 410 nm is produced by the GaN type of semiconductor laser 214.

The excitation light L7 passes through a lens 216 and impinges upon the excitation light guide 401b. The excitation light L7 is guided through the excitation light guide 401b to the leading end of the endoscope 200, passes through the illuminating lens 203, and is irradiated to the region of interest 20.

When the region of interest 20 is exposed to the excitation light L7, the fluorescence L8 is produced from the region of interest 20. The fluorescence L8 is converged by the converging lens 204, transmitted by the excitation light cut filter 208, reflected by the prism 207, transmitted by the color mosaic filter 205, and detected by the CCD image sensor 206.

The imaging of the ordinary image with irradiation of the white light L5 and the imaging of the fluorescence image with irradiation of the excitation light L7 are performed with predetermined timing based on a time-sharing operation. That is to say, the operation for irradiating the white light L5 and exposing the CCD image sensor 206 to the ordinary image and the operation for irradiating the excitation light L7 and exposing the CCD image sensor 206 to the fluorescence image are performed alternately every 1/30 second. In cases where the ordinary image is detected, the output signals of the CCD image sensor 206 are fed into the signal processing circuit 231. In cases where the fluorescence image is detected, the output signals of the CCD image sensor 206 are fed into the signal processing circuit 221.

Therefore, each of the ordinary image and the fluorescence image is acquired every 1/15 second, and an ordinary image and a fluorescence image are displayed on the monitor 260 as dynamic images, which are updated every 1/15 second. The operation timings described above are controlled by the controller 250.

In the signal processing circuit 221, the processing, such as correlative double sampling, clamping, blanking, and amplification, are performed on the signals having been obtained from the CCD image sensor 125. Thereafter, the signal intensity B2 corresponding to the blue wavelength range and the total signal intensity W2 corresponding to the entire wavelength range are calculated from the signal intensities of the complementary color components (i.e., the signal intensity Ye2 of the yellow (or green+red) wavelength range, the signal intensity Cy2 of the cyan (or blue+green) wavelength range, and the signal intensity Mg2 of the magenta (or blue+red) wavelength range). Calculation for any pixel requires use of adjacent pixel values thereof. Specifically, the calculation is carried out using the following equations.

$$W2(Ye2+Cy2+Mg2)/2$$

$$B2=W2-Ye2$$

Further, the pseudo color image signals are calculated from the relative value of the signal intensity B2, i.e., the value of the signal intensity B2 when divided by the total signal intensity W2.

The pseudo color image signals for individual pixels calculated by the signal processing circuit 221 are digitized by the analog-to-digital converting circuit 222. The thus digitized image signals are stored in the fluorescence image memory 223. In accordance with the display timing, the pseudo color image signals having been stored in the fluorescence image memory 223 are subjected to the digital-to-analog conversion in the digital-to-analog converting circuit 224 and transformed by the fluorescence image encoder 225 into predetermined signals. The thus obtained signals are fed into the superimposer 241, and superimposed upon the color image signals representing the ordinary image outputted by the ordinary image memory 232. The superimposed signals are fed into the monitor 260.

The monitor 260 transforms the color image signals and the pseudo color image signals into display signals, and reproduces an ordinary image 40 and a fluorescence image 41 from the display signals.

The fluorescence image 41 is displayed with pseudo colors, such that the display color varies in accordance with the relative value of the signal intensity B2, i.e., the value of the signal intensity B2 when divided by the total signal intensity W2. The pseudo colors for display should preferably be selected such that clear difference may be observed between the display color for the fluorescence produced from the normal tissues and the display color for the fluorescence produced from the diseased tissues. For example, the pseudo colors for display may be selected, so that the fluorescence produced from the normal tissues is displayed in white, and the fluorescence produced from the diseased tissues is displayed in pink or in another color. In such cases, the person, who observes the displayed image, is capable of easily recognizing the state of the diseased tissues.

The fluorescence L8 emitted from the region of interest irradiated with excitation light L7 is separated by the color mosaic filter 205 including the filter elements of complementary colors into the fluorescence components of the yellow (or green+red) wavelength range, the cyan (or blue+green) wavelength, and the magenta (or blue+red) wavelength range. Then, the signal intensity Ye2 of the yellow wavelength range, the signal intensity Cy2 of the cyan wavelength range, and the signal intensity Mg2 of the magenta wavelength range are detected. Thereafter, the signal intensity B2 corresponding to the blue wavelength range and the total signal intensity W2 corresponding to the entire wavelength range are calculated from the above signal intensities of the complementary color components. The fluorescence image is displayed as the pseudo color image based on the relative value of the signal intensity B2, i.e., the value of the signal intensity B2 when divided by the total signal intensity W2. As it is quite rare that the value of the total signal intensity W2 becomes zero, an operation error due to division by the value of zero hardly occurs.

As the fluorescence L8 is separated by the color mosaic filter 205 into the fluorescence components of desired wavelength ranges in the present embodiment, at least two fluorescence components of desired wavelength ranges can be detected using a single detecting means, providing a fluorescence detecting apparatus with a compact configuration requiring a relatively low operation cost. In addition, as a single CCD image sensor obtains both the fluorescence images and the ordinary images, the manufacturing cost of the apparatus can be further reduced.

In addition, as the color mosaic filter 205 in the present embodiment includes filter elements of complementary colors, each fluorescence component of a desired wavelength range can be derived from fluorescence components of wavelength ranges corresponding to the complementary colors, i.e., the fluorescence L8 emitted by the region of interest 20 is used with higher efficiency. Accordingly, the S/N ratio of each fluorescence component can be improved as effects of noises are restrained.

In an alternative to the present embodiment, the signal intensity corresponding to the red wavelength range (the wavelength range of 600 nm or more) may be calculated from the signal intensity Ye2 of the yellow wavelength range, the signal intensity Cy2 of the cyan wavelength range, and the signal intensity Mg2 of the magenta wavelength range. In that case, the fluorescence image is displayed as a pseudo color image based on the relative value of the signal intensity corresponding to the red wavelength range, i.e., the value of the signal intensity corresponding to the red wavelength range when divided by the total signal intensity. As the fluorescence emitted from the diseased tissues and the fluorescence emitted from the normal tissues show different values of the signal intensity corresponding to the red wavelength range, this alternative has the same effect as the second embodiment described above.

Figure 14:
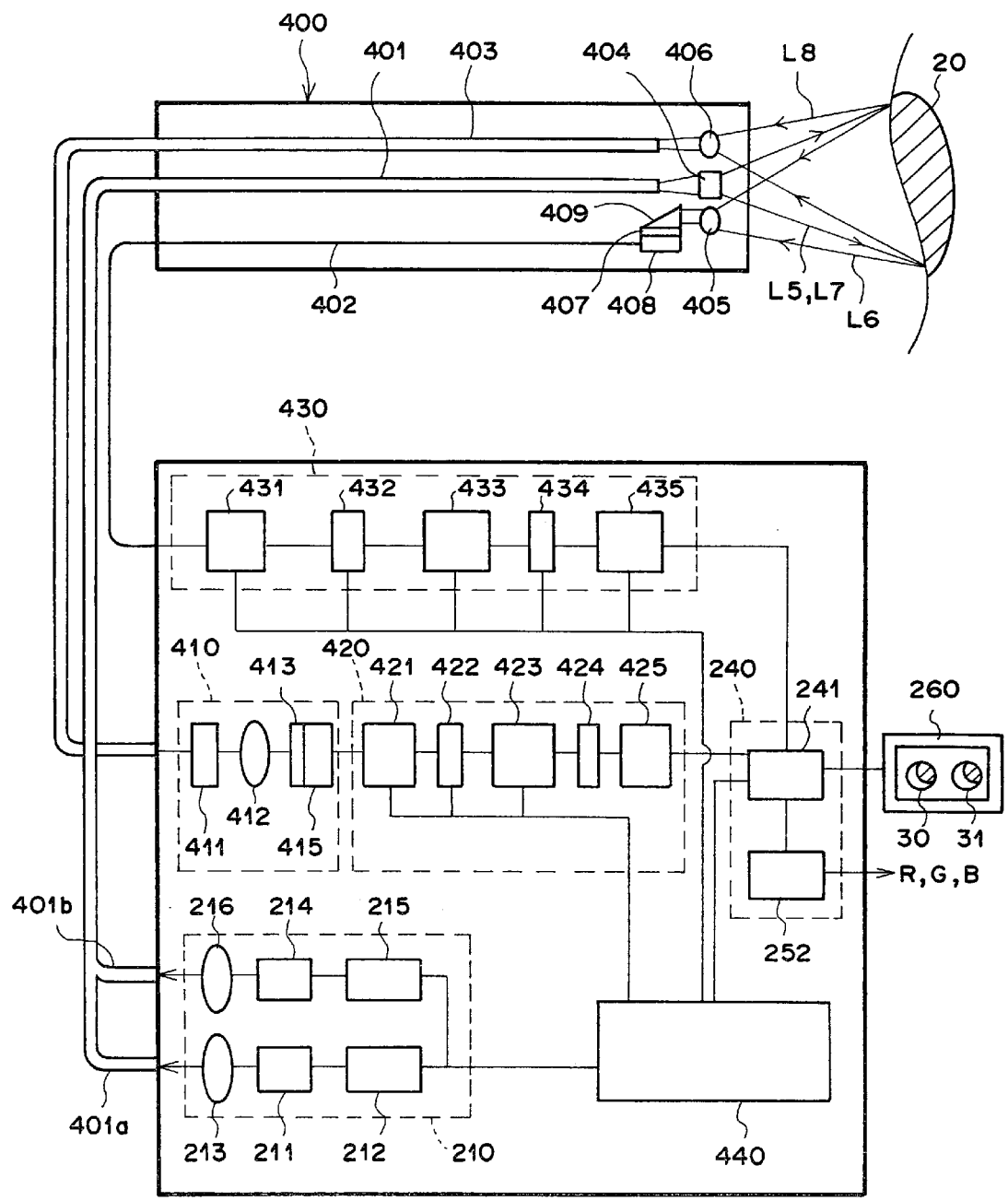
FIG. 14 is a schematic view showing an endoscope system, in which a fluorescence detecting apparatus according to a third embodiment of the present invention is employed.

Now, an endoscope system, in which a third embodiment of the fluorescence detecting apparatus in accordance with the present invention is employed, will be described hereinbelow with reference to FIGS. 14 and 15. FIG. 14 is a schematic view showing the endoscope system, in which the third embodiment of the fluorescence detecting apparatus in accordance with the present invention is employed. In this endoscope system, excitation light is irradiated to a region of interest in a living body, the excitation light causing the region of interest to produce fluorescence. The fluorescence produced from the region of interest is two-dimensionally detected as a fluorescence image using image fibers. The fluorescence image is detected by a charge coupled device (CCD) image sensor provided with a color mosaic filter of a complementary color type fixed thereon, which is constituted of an alternately-arranged array of yellow filter elements for transmitting only fluorescence components covering wavelengths of 510 nm or more and blank elements for transmitting any fluorescence component. Signal intensity of blue fluorescence components covering wavelengths of 510 nm or less and a total signal intensity corresponding to the entire wavelength range are calculated from the intensities of the detected signals. Thereafter, image information is displayed on a monitor as a pseudo color image based on the relative value of the of blue fluorescence components, i.e., the value of the signal intensity of the of blue fluorescence components when divided by the total signal intensity. In FIG. 14, those components similar to the components of the second embodiment shown in FIG. 12 are labeled with the same reference numerals as those in FIG. 12. Descriptions for such components are not repeated in the following.

The endoscope system, in which a third embodiment of the fluorescence detecting apparatus in accordance with the present invention is employed, comprises: an endoscope 400 to be inserted into a region of a patient considered as being a diseased part; and an illuminating unit 210 provided with light sources for producing both white light, which is used when an ordinary image is to be obtained, and the excitation light, which is used when a fluorescence image is to be obtained. The endoscope system also comprises a fluorescence imaging unit 410 for receiving the fluorescence, which is produced from the region of interest in the living body exposed to the excitation light, to detect the image of the fluorescence. The endoscope system further comprises a fluorescence image processing unit 420 for performing image processing for displaying the fluorescence image as a pseudo color image based on a relative value of signal intensity of a specific fluorescence component covering wavelengths falling within a predetermined wavelength range. The endoscope system still further comprises an ordinary image processing unit 430 for performing image processing for displaying an ordinary image as a color image. The endoscope system also comprises a display image processing unit 240 for superimposing the color image of the ordinary image and the pseudo color image of the fluorescence image one upon the other. The endoscope system further comprises a controller 440, which is connected to the respective units to control operation timings. The endoscope system still further comprises a monitor 260 for displaying the ordinary image (i.e., the color image of the ordinary image) and the fluorescence image (i.e., the pseudo color image of the fluorescence image), which have been superimposed one upon the other by the display image processing unit 240.

A light guide 401, a CCD cable 402, and image fibers 403 extend in the endoscope 400 up to a leading end of the endoscope 400. An illuminating lens 404 is located at a leading end of the light guide 401, i.e., at the leading end of the endoscope 400. An objective lens 405 is located at a leading end of the CCD cable 402, i.e., at the leading end of the endoscope 400. The image fibers 403 are glass fibers, and a converging lens 406 is located at a leading end of the image fibers 403. A CCD image sensor 408 is fixed to the leading end of the CCD cable 402. A color mosaic filter 407, which comprises fine band-pass filter elements of three complementary colors arrayed in a mosaic form, is fixed on the CCD image sensor 408. Also, a prism 409 is mounted on the CCD image sensor 408.

The light guide 401 comprises: a white light guide 401a constituted of compound glass fibers; and an excitation light guide 401b constituted of quartz glass fibers. The white light guide 401a and the excitation light guide 401b are bundled together in a cable-like form to constitute the light guide 401. The white light guide 401a and the excitation light guide 401b are connected to the illuminating unit 210. A tail end of the CCD cable 402 is connected to the ordinary image processing unit 430. The tail end of the image fibers 403 is connected to the fluorescence imaging unit 410.

The fluorescence imaging unit 410 comprises an excitation light cut-off filter 411 for filtering out light components covering wavelengths of 430 nm or less, i.e., the wavelengths in the vicinity of the wavelength of the excitation light L3, from fluorescence L4 having passed through the image fibers 403. The fluorescence imaging unit 410 also comprises a CCD image sensor 415, which is constituted of a cooled, back-exposure type of CCD image sensor. The CCD image sensor 415 is provided with a color mosaic filter 413 fixed thereon, which comprises two kinds of small band-pass filter elements arranged in a mosaic-like form.

Figure 15:
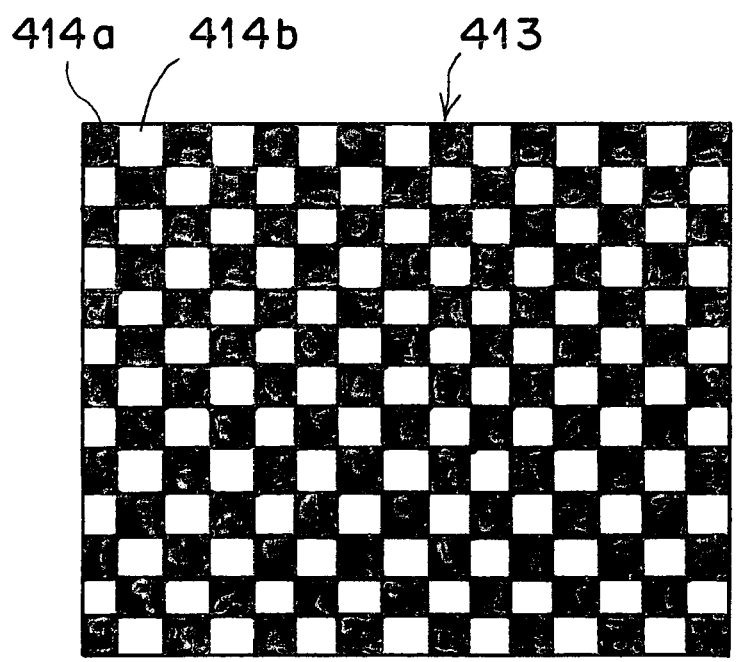
FIG. 15 illustrates a color mosaic filter used in the endoscope system shown in FIG. 14.

As illustrated in FIG. 15, the mosaic filter 413 is constituted of yellow filter elements 414a and blank elements 414b, which are arrayed alternately. The yellow filter elements are small band-pass filters, which transmit only light components covering wavelengths of 510 nm or less. The blank elements 414b transmit any light component. Each of the yellow filter elements 414a and the blank elements 414b corresponds to one of pixels in the CCD image sensor 415.

The fluorescence image processing unit 420 comprises a signal processing circuit 421 for forming pseudo color image signals from the fluorescence image, which has been obtained by the CCD image sensor 415. The fluorescence image processing unit 420 also comprises an analog-to-digital converting circuit 422 for digitizing the pseudo color image signals, which have been obtained from the signal processing circuit 421. The fluorescence image processing unit 420 further comprises a fluorescence image memory 423 for storing the digital pseudo color image signals, which have been obtained from the analog-to-digital converting circuit 422. The fluorescence image processing unit 420 still further comprises a digital-to-analog converting circuit 424 for performing digital-to-analog conversion on the pseudo color image signals, which have been received from the fluorescence image memory 423. The fluorescence image processing unit 420 also comprises a fluorescence image encoder 425 for transforming the pseudo color image signals, which have been received from the digital-to-analog converting circuit 424, into video signals.

The signal processing circuit 421 firstly performs sampling, clamping, blanking, amplification, and the like, on the signals having been obtained from the CCD image sensor 415. Then, the signal processing circuit 421 calculates the signal intensity corresponding to the blue wavelength range and the total signal intensity corresponding to the entire wavelength range. The calculation is based on the signal intensities of the fluorescence components transmitted by the yellow filter elements 414*a* and the blank elements 414*b*, respectively. Thereafter, the signal processing circuit 421 forms the pseudo color image signals based on a relative value of the signal intensity corresponding to the blue wavelength range, i.e., the value of the signal intensity corresponding to the blue wavelength range when divided by the total signal intensity.

The ordinary image processing unit 430 comprises a signal processing circuit 431 for forming color image signals from the ordinary image, which has been detected by the CCD image sensor 408. The ordinary image processing unit 430 also comprises an analog-to-digital converting circuit 432 for digitizing the color image signals, which have been obtained from the signal processing circuit 431. The ordinary image processing unit 430 further comprises an ordinary image memory 433 for storing the digital color image signals, which have been obtained from the analog-to-digital converting circuit 432. The ordinary image processing unit 430 still further comprises a digital-to-analog converting circuit 434 for performing digital-to-analog conversion on the color image signals, which have been received from the ordinary image memory 433. The ordinary image processing unit 430 also comprises an ordinary image encoder 435 for transforming the color image signals, which have been received from the digital-to-analog converting circuit 434, into video signals.

How the endoscope system, in which the third embodiment of the fluorescence detecting apparatus in accordance with the present invention is employed, operates will be described hereinbelow. Firstly, how the endoscope system operates when an ordinary image is to be displayed will be described hereinbelow. When an ordinary image is to be displayed, the electric power source 212 for the white light source 211 is driven in accordance with a control signal fed from the controller 440, so that the white light L5 is produced by the white light source 211. The white light L5 passes through a lens 213 and impinges upon the white light guide 401*a*. The white light L5 is guided through the white light guide 401*a* to the leading end of the endoscope 400, passes through the illuminating lens 404, and is irradiated to a region of interest 10. The white light L5 is reflected as reflected light L6 from the region of interest 10. The reflected light L6 is converged by the objective lens 405 and reflected by the prism 409. The reflected light L6 then passes through the color mosaic filter 407, is received by the CCD image sensor 408, and is photoelectrically converted into electric signals.

In the signal processing circuit 431, the processing, such as correlative double sampling, clamping, blanking, and amplification, are performed on the signals having been obtained from the CCD image sensor 408, in the same manner as in the signal processing circuit 231 of the second embodiment described above. Thereafter, complementary-color/primary-color transform is performed in a pixel-by-pixel manner to calculate signal intensities of primary color components. A color image signal for each pixel is calculated from the signal intensities of primary color components thereof.

The color image signals obtained in the signal processing circuit 431 are then digitized by the analog-to-digital converting circuit 432. The digitized color image signals are stored in the ordinary image memory 433.

In accordance with a display timing, the color image signals having been stored in the ordinary image memory 433 are subjected to the digital-to-analog conversion in the digital-to-analog converting circuit 434 and transformed by the ordinary image encoder 435 into predetermined video signals. The thus obtained video signals are fed into the superimposer 241 and superimposed upon the pseudo color image signals, which are obtained in the manner described later. The superimposed video signals are fed into the monitor 260 and the RGB decoder 242.

Now, how the endoscope system, in which the third embodiment of the fluorescence detecting apparatus in accordance with the present invention is employed, operates when a fluorescence image is to be displayed will be described hereinbelow.

When a fluorescence image is to be displayed, the electric power source 215 for the GaN type of semiconductor laser 214 is driven in accordance with a control signal fed from the controller 440, and the excitation light L7 having a wavelength of 410 nm is produced by the GaN type of semiconductor laser 214. The excitation light L7 passes through a lens 216 and impinges upon the excitation light guide 401*b*. The excitation light L7 is guided through the excitation light guide 401*b* to the leading end of the endoscope 400, passes through the illuminating lens 404, and is irradiated to the region of interest 10.

When the region of interest 10 is exposed to the excitation light L7, the fluorescence L8 is produced from the region of interest 10. The fluorescence L8 is converged by the converging lens 406 and impinges upon the leading end of the image fibers 403. The fluorescence L4 then passes through the image fibers 403 and impinges upon the excitation light cut-off filter 411 of the fluorescence imaging unit 410.

Thereafter, the fluorescence L8 is converged by a lens 412 and passes through the color mosaic filter 413, which is fixed on the CCD image sensor 415. In this manner, an image of the fluorescence L8 is formed on the CCD image sensor 415. Specifically, with the photoelectric conversion performed by the CCD image sensor 415, the image of the fluorescence L8 is converted into electric signals in accordance with the intensity of the fluorescence L8.

In the process circuit 426 of the signal processing circuit 421, the processing, such as correlative double sampling, clamping, blanking, and amplification, are performed on the signals having been obtained from the CCD image sensor 415. The processed signals are fed as two-dimensional signals into the complementary-color/primary-color matrix operation circuit 427. Thereafter, in the complementary-color/primary-color matrix operation circuit 427, a signal intensity B3 of the fluorescence components covering wavelengths falling within the blue wavelength range is calculated for each pixel using the equation $$B3=W3-Ye3$$

wherein Ye3 represents a signal intensity of the fluorescence components covering wavelengths falling within the yellow wavelength range (i.e., green+red) which have passed through the yellow filter elements 414a, and W3 represents a total signal intensity corresponding to the entire wavelength range which have passed through the blank elements 414b. The calculation for each pixel is performed using the signal intensities for pixels adjacent to that pixel.

Pseudo color image signals are calculated based on a relative value of the signal intensity B3, i.e., the value of the signal intensity B3 when divided by the total signal intensity W3. The pseudo color image signals, which are made up of pseudo color image signal components corresponding to respective pixels and have been obtained from the signal processing circuit 421, are digitized by the analog-to-digital converting circuit 422. The thus digitized pseudo color image signals are stored in the fluorescence image memory 423. In accordance with the display timing, the pseudo color image signals having been stored in the fluorescence image memory 423 are subjected to the digital-to-analog conversion in the digital-to-analog converting circuit 424, and transformed by the fluorescence image encoder 425 into predetermined video signals. The thus obtained video signals are fed from the fluorescence image encoder 425 to the superimposer 241. In the superimposer 241, the pseudo color image signals are superimposed upon the color image signals, which represent the ordinary image and which have been received from the ordinary image encoder 435. The thus obtained video signals are fed into the monitor 260 and the RGB decoder 241.

The monitor 260 transforms the color image signals and the pseudo color image signals, which have been received as the video signals, and to reproduce an ordinary image 30 and a fluorescence image 31. The fluorescence image 41 is displayed with pseudo colors, such that the display color varies in accordance with the relative value of the signal intensity B3, i.e., the value of the signal intensity B3 when divided by the total signal intensity W3. The pseudo colors for display should preferably be selected such that clear difference can be observed between the display color for the fluorescence produced from the normal tissues and the display color for the fluorescence produced from the diseased tissues. For example, the pseudo colors for display may be selected so that the fluorescence produced from the normal tissues is displayed in white, and the fluorescence produced from the diseased tissues is displayed in pink or in another color.

In such cases, the person, who observes the displayed image, can easily recognize the state of the diseased tissues.

The series of operations described above are controlled by the controller 440. The irradiation of the white light L5 and the exposure of the CCD image sensor 408 to the reflected light L6 are performed synchronously every 1/30 second. Their radiation of the excitation light L7 and the exposure of the CCD image sensor 415 to the fluorescence L8 are performed during a period in which the irradiation of the white light L5 is ceased, i.e. during a period corresponding to a vertical blanking period in a television system. Therefore, the detection of the ordinary image is not obstructed by the detection of the fluorescence image. Also, since each of the ordinary image and the fluorescence image is detected every 1/30 second, the ordinary image 30 and the fluorescence image 31 are displayed on the monitor 260 as dynamic images, which are updated every 1/30 second.

As the fluorescence L8 emitted from the region of interest 10 irradiated with excitation light L7 goes through the color mosaic filter 413 including yellow filter elements 414b and blank elements 414b, the signal intensity Ye3 of the yellow (or green+red) wavelength range and the total signal intensity W3 of the entire wavelength range can be obtained. Thereafter, the signal intensity B3 corresponding to the blue wavelength range of 510 nm or less is calculated from the above signal intensities Ye3 and W3. The fluorescence image is displayed as the pseudo color image based on the relative value of the signal intensity B3, i.e., the value of the signal intensity B3 when divided by the total signal intensity W3. As it is quite rare that the value of the total signal intensity W3 becomes zero, an operation error due to division by the value of zero hardly occurs.

As the fluorescence L8 is separated by the color mosaic filter 413 into two fluorescence components of desired wavelength ranges in the present embodiment, the two fluorescence components of desired wavelength ranges can be detected using a single detecting means, providing a fluorescence detecting apparatus with a compact configuration requiring a relatively low operation cost.

In addition, as the color mosaic filter 413 in the present embodiment includes filter elements of complementary colors, each fluorescence component of a desired wavelength range can be derived from fluorescence components of wavelength ranges corresponding to the complementary colors, i.e., the fluorescence L8 emitted by the region of interest 10 is used with higher efficiency. Accordingly, the S/N ratio of each fluorescence component can be improved as effects of noises are restrained.

In an alternative to the present embodiment, the color mosaic filter fixed on the CCD image sensor may include blue filter elements and blank elements arranged alternately. The blue filter elements transmit those fluorescence components having the wavelengths of 510 nm or less. Using the color mosaic filter of such a configuration, a pseudo color image may be derived based on a relative value of the signal intensity corresponding to the blue wavelength range, i.e., the value of the signal intensity corresponding to the blue wavelength range when divided by the total signal intensity.

In another alternative to the present embodiment, the color mosaic filter fixed on the CCD image sensor may include cyan filter elements and blank elements arranged alternately. The cyan (or blue+green) filter elements transmit those fluorescence components having the wavelengths of 600 nm or less. Using the color mosaic filter of such a configuration, signal intensity corresponding to the red wavelength range (i.e., 600 nm or more) maybe calculated from the signal intensity corresponding to the cyan wavelength range and the total signal intensity. Then, a pseudo color image may be derived based on a relative value of the signal intensity corresponding to the red wavelength range, i.e., the value of the signal intensity corresponding to the red wavelength range when divided by the total signal intensity. As the fluorescence emitted from the diseased tissues and the fluorescence emitted from the normal tissues show different values of the signal intensity corresponding to the red wavelength range, this alternative has the same effect as the third embodiment described above. The cyan filter elements may be replaced by red filter elements, so that the signal intensity corresponding to the red wavelength range can directly be obtained.

Although the fluorescence image in the second and third embodiments described above is displayed as the pseudo color image based on division values between the signal intensities of two fluorescence components covering different wavelength ranges, various other styles of display are also applicable. For example, the displayed fluorescence image may be a direct division image of division values between the signal intensities of two fluorescence components covering different wavelength ranges. Otherwise, the displayed fluorescence image may be a comparison image comparing the obtained division values with standard division values derived from the fluorescence emitted from standard normal tissues and standard diseased tissues. It is also possible to display an image of relative signal intensity of a fluorescence component covering a selected wavelength range according to additive processes.

Figure 16:
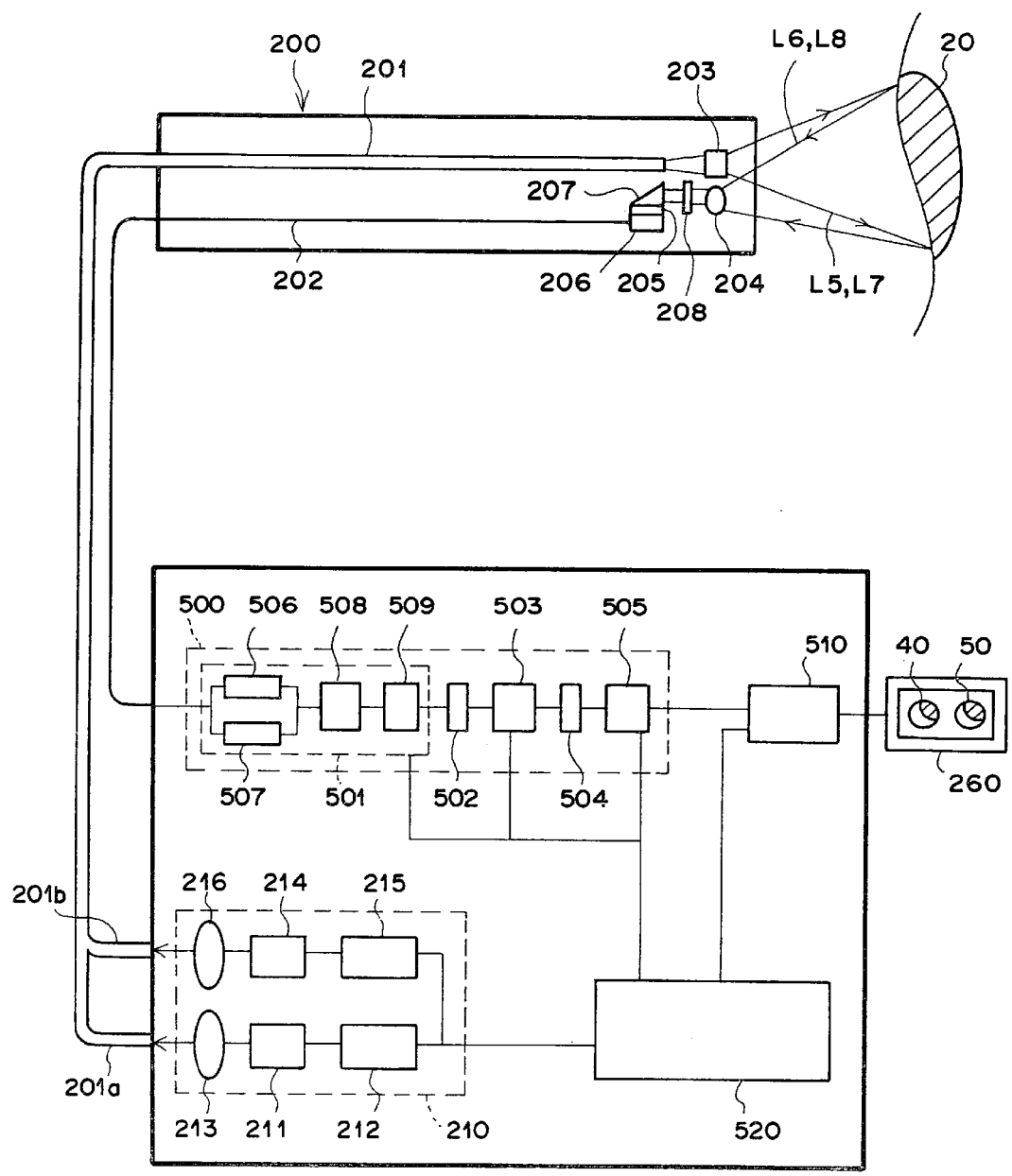
FIG. 16 is a schematic view showing an endoscope system, in which a fluorescence detecting apparatus according to a fourth embodiment of the present invention is employed.

Now, an endoscope system, in which a fluorescence detecting apparatus according to the fourth embodiment of the present invention is employed, will be described hereinbelow with reference to FIG. 16. In FIG. 16, those components similar to the components of the second embodiment shown in FIG. 12 are labeled with the same reference numerals as those in FIG. 12. Descriptions for such components are not repeated in the following. FIG. 16 is a schematic view showing the endoscope system, in which the fluorescence detecting apparatus according to the fourth embodiment of the present invention is employed.

In this endoscope system, excitation light is irradiated to a region of interest in a living body. Fluorescence produced from the region of interest is received by a CCD image sensor, which is located at a leading end of an endoscope and which is utilized also for detecting an ordinary image. In this manner, a detected fluorescence image is displayed on the monitor as a color image.

This endoscope system comprises: an endoscope 200 to be inserted into a region of a patient considered as being a diseased part;

and an illuminating unit 210 provided with light sources for producing white light, which is used when an ordinary image is to be displayed, and excitation light, which is used when a fluorescence image is to be displayed. The endoscope system also comprises an image processing unit 500 for performing image processing for displaying fluorescence images and ordinary images.

The endoscope system further comprises a superimposer 510 for superimposing the ordinary image and the fluorescence image one upon the other. The endoscope system still further comprises a controller 520, which is connected to the respective units and the superimposer 510 for controlling operation timings. The endoscope system also comprises the monitor 260 for displaying the fluorescence images and the ordinary images with colors.

The image processing unit 500 comprises a signal processing circuit 501 for forming color image signals from a fluorescence image or an ordinary image, which have been detected by the CCD image sensor 206. The image processing unit 500 also comprises an analog-to-digital converting circuit 502 for digitizing the color image signals, which have been obtained from the signal processing circuit 501. The image processing unit 500 further comprises an image memory 503 for storing the digital color image signals, which have been obtained from the analog-to-digital converting circuit 502. The image processing unit 500 still further comprises a digital-to-analog converting circuit 504 for performing digital-to-analog conversion on the color image signals, which have been received from the image memory 503. The image processing unit 500 also comprises an encoder 505 for transforming the color image signals, which have been received from the digital-to-analog converting circuit 504, into video signals.

The signal processing circuit 501 comprises an ordinary image process circuit 506 for performing the processing, such as double sampling, amplification, and clamping, on signals in cases where the ordinary image is detected by the CCD image sensor 206. The signal processing circuit 501 also comprises a fluorescence image process circuit 507 for performing the processing on signals in cases where the fluorescence image is detected by the CCD image sensor 206. The signal processing circuit 501 further comprises a complementary-color/primary-color matrix operation circuit 508 for calculating the signal intensities representing three primary colors from the signal intensities of the fluorescence components transmitted by the yellow filter elements 205a, the cyan filter elements 205b and the blank elements 205c. The signal processing circuit 501 further comprises an image signal matrix operation circuit 509 for forming the color image signals from the signal intensities representing three primary colors having been calculated by the complementary-color/primary-color matrix operation circuit 508.

How the endoscope system, in which the fluorescence detecting apparatus according to the fourth embodiment of the present invention is employed, operates will be described hereinbelow. Firstly, how the endoscope system operates when an ordinary image is to be displayed will be described hereinbelow. When an ordinary image is to be displayed, the electric power source 212 for the white light source 211 is driven in accordance with a control signal fed from the controller 520, so that the white light L5 is produced by the white light source 211 and irradiated to the region of interest 20. The reflected light L6 of the white light L5 passes through the mosaic filter 205 and is received by the CCD image sensor 206.

In the ordinary image process circuit 506 of the signal processing circuit 501, the processing is performed on the signals having been obtained from the CCD image sensor 206. Thereafter, in the same manner as in the signal processing circuit 231 of the second embodiment described above, the complementary-color/primary-color matrix operation circuit 508 calculates the signal intensity B4 of the blue wavelength components of the reflected light L6, the signal intensity G4 of the green wavelength components of the reflected light L6 and the signal intensity R4 of the red wavelength components of the reflected light L6, for each pixel with the matrix operations. The calculation is carried out using the signal intensity Ye4 of the yellow wavelength components covering wavelengths falling within the yellow wavelength range (i.e., green+red), the signal intensity Cy4 of the cyan wavelength components covering wavelengths falling within the cyan wavelength range (i.e., blue+green), and the signal intensity Mg4 of the magenta wavelength components covering wavelengths falling within the magenta wavelength range (i.e., blue+red) The matrix operation for each pixel is performed using the signal intensities for pixels adjacent to that pixel. Further, the image signal matrix operation circuit 508 performs another set of matrix operations on the signal intensities B4, G4 and R4 representing the three primary colors to derive the luminance signal Y4 and the color difference signals R4-Y4 and B4-Y4, which act as the color image signals according to the NTSC method.

The color image signals (i.e., the luminance signal Y4 and the color difference signals R4-Y4 and B4-Y4), which are made up of color image signal components corresponding to respective pixels and which have been obtained from the signal processing circuit 501, are digitized by the analog-to-digital converting circuit 502. The thus obtained color image signals are stored in an ordinary image storage area of the image memory 503. In accordance with the display timing, the color image signals, which represent the ordinary image and which have been stored in the image memory 503, are subjected to the digital-to-analog conversion in the digital-to-analog converting circuit 504, and transformed by the encoder 505 into predetermined video signals. The thus obtained video signals are fed from the encoder 505 into the superimposer 510. In the superimposer 510, the color image signals are superimposed upon another set of color image signals, which represent the fluorescence image and are formed in the manner described later. The superimposed image signals are fed into the monitor 260.

Now, how the endoscope system, in which the fluorescence detecting apparatus according to the fourth embodiment of the present invention is employed, operates when a fluorescence image is to be displayed will be described hereinbelow.

When a fluorescence image is to be displayed, the electric power source 215 for the GaN type of semiconductor laser 214 is driven in accordance with a control signal fed from the controller 520, so that the excitation light L7 having a wavelength of 410 nm is produced by the GaN type of semiconductor laser 214. The excitation light L7 is irradiated to the region of interest 20.

When the region of interest 20 is exposed to the excitation light L7, fluorescence L8 is produced from the region of interest 20. The fluorescence L8 passes through the color mosaic filter 205 and is received by the CCD image sensor 206.

As in the second embodiment described above, the timings, with which the imaging of the ordinary image with irradiation of the white light L5 and the imaging of the fluorescence image with irradiation of the excitation light L7 are performed alternately, are controlled by the controller 520 and performed in accordance with the timing chart illustrated in FIG. 9. As illustrated in FIG. 9, the operation for irradiating the white light L5 and exposing the CCD image sensor 206 to the ordinary image and the operation for irradiating the excitation light L7 and exposing the CCD image sensor 206 to the fluorescence image are performed alternately every 1/30 second. In accordance with control signals given by the controller 520, the signals obtained from the detection of the ordinary image are fed into the ordinary image process circuit 506, and the signals obtained from the detection of the fluorescence image are fed into the fluorescence image process circuit 507.

Therefore, each of the ordinary image and the fluorescence image is acquired every 1/15 second, and the ordinary image and a fluorescence image are displayed on the monitor 260 as dynamic images, which are updated every 1/15 second.

In the fluorescence image process circuit 507 of the signal processing circuit 501, the processing is performed on the signals having been obtained from the CCD image sensor 206.

Thereafter, as in cases where the ordinary image is detected, the complementary-color/primary-color matrix operation circuit 508 calculates a signal intensity B4 of the blue wavelength components of the fluorescence L8, a signal intensity G4 of the green wavelength components of the fluorescence L8, and a signal intensity R4 of the red wavelength components of the fluorescence L8, for each pixel with the matrix operations. The calculation is carried out using a signal intensity Ye4 of the yellow wavelength components of the fluorescence L8, a signal intensity Cy4 of the cyan wavelength components of the fluorescence L8, and a signal intensity Mg4 of the magenta wavelength components of the fluorescence L8. Further, in the image signal matrix operation circuit 508, another set of matrix operations according to the NTSC method are performed using the signal intensities B4, G4 and R4 of the three primary colors to derive a luminance signal Y4 and color difference signals R4-Y4 and B4-Y4, which act as the color image signals.

The color image signals (i.e., the luminance signal Y4 and the color difference signals R4-Y4 and B4-Y4), which are made up of color image signal components corresponding to respective pixels and which have been obtained from the signal processing circuit 501, are digitized by the analog-to-digital converting circuit 502. The thus digitized color image signals are stored in a fluorescence image storage area of the image memory 503. In accordance with the display timing, the color image signals, which represent the fluorescence image and which have been stored in the image memory 503, are subjected to the digital-to-analog conversion in the digital-to-analog converting circuit 504, and transformed by the encoder 505 into predetermined signals. The thus obtained signals are fed from the encoder 505 to the superimposer 510. In the superimposer 510, the color image signals are superimposed upon the color image signals representing the ordinary image (i.e., the luminance signal Y4 and the color difference signals R4-Y4 and B4-Y4), which have been received from the image memory 503. The superimposed image signals are fed into the monitor 260.

The monitor 260 transforms the color image signals representing the ordinary image and the color image signals representing the fluorescence image to display the ordinary image 40 and the fluorescence image 50.

Therefore, in the fluorescence image 50, as in the cases of the ordinary image 40, the signal intensity B4 of the wavelength range of 430 nm to 510 nm is displayed as the color signal B, the signal intensity G4 of the wavelength range of 510 nm to 600 nm is displayed as the color signal G, and the signal intensity R4 of the wavelength range of 600 nm to 700 nm is displayed as the color signal R. In this manner, the fluorescence image 50 is displayed like an ordinarily formed color image. Accordingly, the display color for the fluorescence produced from the normal tissues is cyan, and the display color for the fluorescence produced from the diseased tissues is a color close to white. Thus, the same effects as those with the second embodiment shown in FIG. 6 can be obtained. Further, a fine difference between the signal intensities corresponding to individual wavelength ranges of the fluorescence produced from the region of interest can be observed as a difference in tint.

In the fourth embodiment described above, employed as the coefficients in the matrix operations for transforming the three primary color signals B4, G4 and R4 into the color image signals in the image signal matrix operation circuit 508 are the coefficients utilized in ordinary matrix operations according to the NTSC method. Alternatively, different coefficients in the matrix operations may be selected to set the tint corresponding to each signal intensity arbitrarily.

As the fluorescence L8 is separated by the color mosaic filter 205 into the fluorescence components of desired wavelength ranges in the present embodiment, at least two fluorescence components of desired wavelength ranges can be detected using a single detecting means, providing a fluorescence detecting apparatus with a compact configuration requiring a relatively low operation cost.

In addition, as the color mosaic filter 205 in the present embodiment includes filter elements of complementary colors, each fluorescence component of a desired wavelength range can be derived from fluorescence components of wavelength ranges corresponding to the complementary colors, i.e., the fluorescence L8 emitted by the region of interest 20 is used with higher efficiency. Accordingly, the S/N ratio of each fluorescence component can be improved as effects of noises are restrained.

Although the color mosaic filter 205 in the embodiment described above includes alternately-arranged yellow filter elements 205a, cyan filter elements 205b and magenta filter elements 205c, a color mosaic filter of any kind may instead be used as far as the signal intensities of the three primary colors are obtainable from the signal intensities of the light components detected through the color mosaic filter. For example, the color mosaic filter may include alternately-arranged yellow filter components, cyan filter components and blank components. Otherwise, the color mosaic filter may be of a primary color type including red filter components, green filter components and blue filter components. Also, the specific wavelength range covered by each filter element may desirably be changed.

What is claimed is:

1. A fluorescence detecting apparatus, comprising:
   i) an excitation light irradiating means for irradiating excitation light to a region of interest in a living body to which a fluorescent diagnosis drug, that is capable of producing fluorescence when excited with said excitation light has been administered, said excitation light covering wavelengths falling within an excitation wavelength range for said fluorescent diagnosis drug and an intrinsic dye in the living body, said intrinsic dye being capable of producing fluorescence when excited with the excitation light,
   ii) a fluorescence detecting means for detecting first and second fluorescence components,
   said first fluorescence component being either one of:
      a) an entire fluorescence component covering wavelengths falling within a wavelength range which contains: a wavelength range of extrinsic fluorescence produced by said fluorescent diagnosis drug in said region of interest in the living body, and a wavelength range of intrinsic fluorescence produced by said intrinsic dye in said region of interest in the living body, and
      b) a fluorescence sum component which is the sum of:
   a fluorescence component covering wavelengths falling within a part of the wavelength range of the extrinsic fluorescence produced by said fluorescent diagnosis drug in said region of interest in the living body, and a fluorescence component covering wavelengths falling within a part of the wavelength range of the intrinsic fluorescence produced by said intrinsic dye in the living body, and
   said second fluorescence component being either one of:
      a) a fluorescence component covering wavelengths falling within a part of the wavelength range of the extrinsic fluorescence, and
      b) a fluorescence difference component which is the difference between: a fluorescence component covering wavelengths falling within a part of the wavelength range of the extrinsic fluorescence, and a fluorescence component covering wavelengths falling within a part of the wavelength range of the intrinsic fluorescence, and
   iii) a division means for carrying out a division operation between the first fluorescence component and the second fluorescence component, wherein
   the fluorescence detecting means comprises:
   a color mosaic filter for separating the fluorescence emitted from the region of interest into the first fluorescence component and the second fluorescence component, and
   a detecting means for detecting the first and second fluorescence components in a two-dimensional manner, and wherein
   the color mosaic filter is fixed on a fluorescence detecting surface of the detecting means.

2. A fluorescence detecting apparatus according to claim 1, wherein the color mosaic filter includes filter elements of primary colors.

3. A fluorescence detecting apparatus according to claim 1, wherein the color mosaic filter includes filter elements of complementary colors.

4. A fluorescence detecting apparatus, comprising:
   i) an excitation light irradiating means for irradiating excitation light to a region of interest in a living body, said excitation light covering wavelengths falling within an excitation wavelength range for an intrinsic dye in the living body, said intrinsic dye being capable of producing fluorescence when excited with the excitation light,
   ii) a fluorescence detecting means for detecting first and second fluorescence components,
   said first fluorescence component being either one of:
      a) an entire intrinsic fluorescence component covering wavelengths falling within a visible wavelength range, which contains a comparatively short wavelength range and a comparatively long wavelength range among a wavelength range of intrinsic fluorescence produced by said intrinsic dye in said region of interest in the living body, and
      b) a fluorescence sum component which is the sum of:
      a fluorescence component covering wavelengths falling within a part of the comparatively short wavelength range among the wavelength range of the intrinsic fluorescence produced by said intrinsic dye in said region of interest in the living body, and a fluorescence component covering wavelengths falling within a part of the comparatively long wavelength range among the wavelength range of the intrinsic fluorescence, and
   said second fluorescence component being either one of:
      a) a fluorescence component covering wavelengths falling within a part of the comparatively long wavelength range among the wavelength range of the intrinsic fluorescence, and
      b) a fluorescence difference component, which is the difference between: a fluorescence component covering wavelengths falling within a part of the comparatively short wavelength range among the wavelength range of the intrinsic fluorescence, and a fluorescence component covering wavelengths falling within a part of the comparatively long wavelength range among the wavelength range of the intrinsic fluorescence, and
   iii) a division means for carrying out a division operation between the first fluorescence component and the second fluorescence component, wherein the fluorescence detecting means comprises:

a color mosaic filter for separating the fluorescence emitted from the region of interest into the first fluorescence component and the second fluorescence component, and a detecting means for detecting the first and second fluorescence components in a two-dimensional manner, and wherein the color mosaic filter is fixed on a fluorescence detecting surface of the detecting means.

5. A fluorescence detecting apparatus according to claim 4, wherein the color mosaic filter includes filter elements of primary colors.

6. A fluorescence detecting apparatus according to claim 4, wherein the color mosaic filter includes filter elements of complementary colors.

7. A fluorescence detecting apparatus, comprising:
i) an excitation light irradiating means for irradiating excitation light to a region of interest in a living body,
ii) a fluorescence detecting means for detecting at least two fluorescence components of desired wavelength ranges extracted from fluorescence emitted from the region of interest irradiated with the excitation light, and
iii) a signal processing means for processing in a predetermined manner signals representing said at least two fluorescence components detected by the fluorescence detecting means, wherein the fluorescence detecting means comprises:

a color mosaic filter for separating the fluorescence emitted from the region of interest into said at least two fluorescence components and a detecting means for detecting said at least two fluorescence components in a two-dimensional manner, and wherein the color mosaic filter is fixed on a fluorescence detecting surface of the detecting means.

8. A fluorescence detecting apparatus according to claim 7, wherein the color mosaic filter includes filter elements of primary colors.

9. A fluorescence detecting apparatus according to claim 7, wherein the color mosaic filter includes filter elements of complementary colors.

* * * * *